US012649949B2

(12) United States Patent
Cherfils et al.

(10) Patent No.: US 12,649,949 B2
(45) Date of Patent: Jun. 9, 2026

(54) METHODS AND COMPOSITIONS FOR TREATING CELL SENESCENCE ACCUMULATION RELATED DISEASE

(71) Applicants: INSERM (INSTITUT NATIONAL DE LA SANTÉ ET DE LA RECHERCHE MÉDICALE), Paris (FR); CENTRE NATIONAL DE LA RECHERCHE SCIENTIFIQUE (CNRS), Paris (FR); UNIVERSITE COTE D'AZUR, Nice (FR)

(72) Inventors: Julien Cherfils, Nice (FR); Eric Gilson, Nice (FR); Charlene Iltis, Nice (FR)

(73) Assignees: INSERM (INSTITUT NATIONAL DE LA SANTÉ ET DE LA RECHERCHE MÉDICALE), Paris (FR); CENTRE NATIONAL DE LA RECHERCHE SCIENTIFIQUE (CNRS), Paris (FR); UNIVERSITE COTE D'AZUR, Nice (FR); CENTRE HOSPITALIER UNIVERSITAIRE DE NICE, Nice (FR)

( * ) Notice: Subject to any disclaimer, the term of this patent is extended or adjusted under 35 U.S.C. 154(b) by 418 days.

(21) Appl. No.: 18/556,472

(22) PCT Filed: Apr. 22, 2022

(86) PCT No.: PCT/EP2022/060713

§ 371 (c)(1),
(2) Date: Oct. 20, 2023

(87) PCT Pub. No.: WO2022/223791

PCT Pub. Date: Oct. 27, 2022

(65) Prior Publication Data

US 2024/0158861 A1 May 16, 2024

Related U.S. Application Data

(60) Provisional application No. 63/178,738, filed on Apr. 23, 2021.

(30) Foreign Application Priority Data

May 11, 2021 (EP) .................................... 21305607

(51) Int. Cl.
*C12Q 1/68* (2018.01)
*C12Q 1/6851* (2018.01)
(Continued)

(52) U.S. Cl.
CPC ......... *C12Q 1/6883* (2013.01); *C12Q 1/6851* (2013.01); *G01N 33/6893* (2013.01); *C12Q 2600/158* (2013.01)

(58) Field of Classification Search
CPC ........................................................ C12Q 1/68
See application file for complete search history.

(56) References Cited

U.S. PATENT DOCUMENTS

2004/0092438 A1* 5/2004 Martin-Villalba ........................... A61K 31/5375 514/17.8
2006/0188975 A1* 8/2006 Ramaswami ........ A61K 48/005 435/368
(Continued)

OTHER PUBLICATIONS

Copani et al, β-Amyloid-Induced Synthesis of the Ganglioside Gd3 is a Requisite for Cell Cycle Reactivation and Apoptosis in Neurons, J Neurosci. May 15, 2002;22(10):3963-3968. doi: 10.1523/JNEUROSCI.22-10-03963.2002.*
(Continued)

*Primary Examiner* — Aaron A Priest
(74) *Attorney, Agent, or Firm* — WCF IP

(57) ABSTRACT

The inventors have surprisingly demonstrated that GD3 positive senescent cells inhibit NK cell in vitro and in vivo while GD3 negative senescent cells is associated with NK cell functionality, both with human or murine cells. The inventors' results bring the proof of concept that GD3
(Continued)

Figures 1A, 1B:
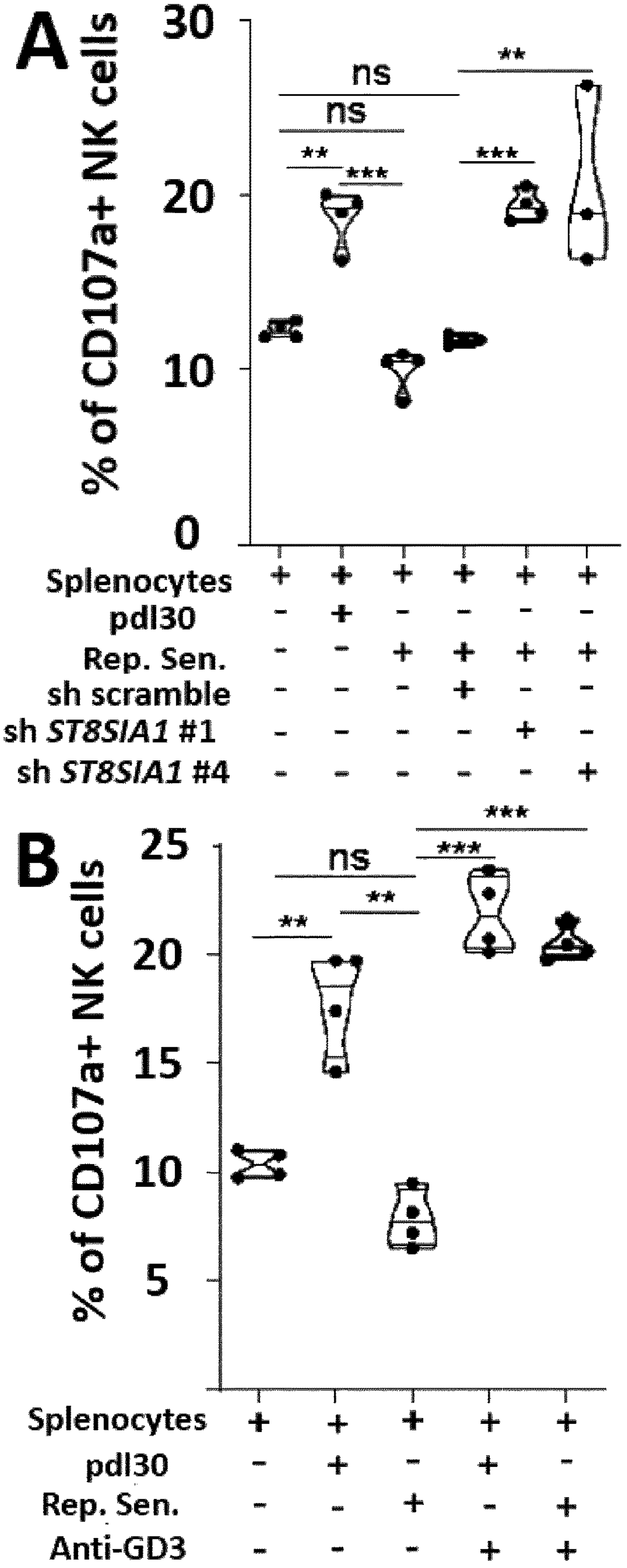

expression may represent a Senescence-associated Immune Checkpoint (SIC) that determines senescent cell immunogenicity and identify GD3 and more generally SIC as a multi-hit target for age-associated diseases. Thus, GD3 may be a major step forward in the development of efficient anti-senescence immunotherapies. In particular, the present invention relates to a method for identifying whether a cell is in senescence process comprising the steps of: i) measuring the co-expression level of ST8Sia1 (GD3) with a senescence marker in a biological sample; ii) comparing the co-expression level measured at step i) with its predetermined reference value, and iii) concluding that the cell is in senescence process when the co-expression level of GD3 with a senescence marker is higher than its predetermined reference value or concluding that cell is not in senescence process when the co-expression level of GD3 with a senescence marker is lower or similar than its predetermined reference value. The present invention also relates a method for treating senescent cells accumulation related disease in a subject in need thereof, comprising administering to said subject a therapeutically effective amount of a GD3 inhibitor.

10 Claims, 7 Drawing Sheets

Specification includes a Sequence Listing.

(51) Int. Cl.

| | |
|---|---|
| ***C12Q 1/6883*** | (2018.01) |
| ***G01N 33/68*** | (2006.01) |

(56) References Cited

U.S. PATENT DOCUMENTS

| | | | | |
|---|---|---|---|---|
| 2011/0165566 | A1* | 7/2011 | Wittliff | C12Q 1/6886 435/6.11 |
| 2023/0330267 | A1* | 10/2023 | Cao | A61K 38/1841 |
| 2024/0100076 | A1* | 3/2024 | Yu | A61P 25/28 |

OTHER PUBLICATIONS

Hampel B et al, "Differential regulation of apoptotic cell death in senescent human cells", Experimental Gerontology, Elsevier, Amsterdam, NL,vol. 39, No. 11-12, Nov. 1, 2004 (Nov. 1, 2004), p. 1713-1721.

Florence Debacq-Chainiaux et al, "Differential regulation of apoptotic cell death in senescent human cells", Nature Protocols, vol. 4, No. 12, Nov. 19, 2009 (Nov. 19, 2009), p. 1798-1806.

Mirzayans Razmik et al, "Role of p16INK4A in Replicative Senescence and DNA Damage-Induced Premature Senescence in p53-Deficient Human Cells", US Jan. 1, 2012 (Jan. 1, 2012), vol. 2012, p. 1-8.

Shay Jerry W. et al, "Senescence and immortalization: role of telomeres and telomerase", GB May 1, 2005 (May 1, 2005), vol. 26, No. 5, p. 867-874.

Shtutman Michael et al, "Cellular Model of p21-Induced Senescence", "Clinical Applications of PCR", p. 31-39, Nov. 4, 2016 (Nov. 4, 2016), New York, NYSpringer New York.

* cited by examiner

METHODS AND COMPOSITIONS FOR TREATING CELL SENESCENCE ACCUMULATION RELATED DISEASE

FIELD OF THE INVENTION

The invention is in the field of immunotherapy. More particularly the invention relates to methods and compositions for use in the prevention or treatment cell senescence accumulation related disease in a subject in need thereof. The present invention also relates to diagnosis or prognosis methods of cell

BACKGROUND OF THE INVENTION

Senescent cells accumulate in aging tissues and their elimination improves healthy aging[1-4]. Therefore, therapeutic interventions targeting cellular senescence emerge as promising strategies for delaying or potentially reversing a vast range of age-related diseases[5]. Since components of the immune system were shown to be responsible for senescent cell elimination[6-11], an anti-aging option could be to specifically activate the immune system to induce senescent cell clearance. Strikingly, the inventors unveil here that senescent cells, triggered by different types of stressors apart from oncogenic activation, exhibited immune escape toward Natural Killer (NK) cells that may limit the use of anti-senescence immunotherapies. They further show by mass spectrometry that senescent cells reshuffle their ganglioside composition by an important increase of the ganglioside GD3. This resulted from the upregulation upon senescence entry of the transcription of the gene encoding the ST8SIA1 enzyme responsible for GD3 synthesis. GD3 upregulation in senescent cells leads to a strong immunosuppressive signal for NK cells mediated immunosurveillance. The inventor's results demonstrate that GD3 expression determines the switch from immune clearance towards immune escape of senescent cells, thus regulating their accumulation rate. Consistently, in a mouse model of lung fibrosis, senescent cell dependent NK cell immunosuppression is blunted in vivo using anti-GD3 mAbs with a clear anti fibrotic effect. Therefore, the inventor propose that GD3 expression behaves as a senescence associated immune checkpoint that limit their elimination by the immune system. Targeting GD3 by specific antibodies may be a major step forward in the development of efficient anti-senescence immunotherapies.

SUMMARY OF THE INVENTION

The invention relates to methods and compositions for use in the prevention or treatment cell senescence accumulation related disease in a subject in need thereof. The present invention also relates to diagnosis or prognosis methods of cell senescence accumulation related disease in a patient from a biological sample of said patient. In particular, the present invention is defined by the claims.

DETAILED DESCRIPTION OF THE INVENTION

The inventors have surprisingly demonstrated that GD3 positive cells inhibit NK cell in vitro and in vivo while GD3 negative is associated with NK cell functionality, both with human or murine cells. The inventors' results bring the proof of concept that GD3 expression may represent a Senescence associated Immune Checkpoint (SIC) that determines senescent cell immunogenicity and identify GD3 and more generally SIC as a multi-hit target for age-associated diseases. Thus, GD3 may be a major step forward in the development of efficient anti-senescence immunotherapies.

Method of Identification and of Diagnostic

In a first embodiment, the present invention relates to a method for identifying whether a cell is in senescence process comprising the steps of: i) measuring the co-expression level of ST8Sia1 (GD3) with a senescence marker in a biological sample; ii) comparing the co-expression level measured at step i) with its predetermined reference value, and iii) concluding that the cell is in senescence process when the co-expression level of GD3 with a senescence marker is higher than its predetermined reference value or concluding that cell is not in senescence process when the co-expression level of GD3 with a senescence marker is lower or similar than its predetermined reference value.

In some embodiments, the method of the present invention comprises the step of comparing the determined co-expression level of GD3 associated with a senescence marker with a predetermined reference value.

In some embodiment, the cell is in senescence process when the co-expression level of GD3 with a senescence marker is higher than its predetermined reference value.

In some embodiment, the cell is not in senescence process when the co-expression level of GD3 with a senescence marker is lower or similar than its predetermined reference value.

In a second embodiment, the present invention relates to a method for diagnosing senescent cells accumulation related disease in a subject comprising i) detecting the co-expression of ST8Sia1 (GD3) with a senescence marker in a biological sample obtained from a subject and ii) and concluding that the subject suffers from a senescent cells accumulation related disease when the co-expression of GD3 with senescence marker is detected in the biological sample.

As used herein, the term "ganglioside" refers to a molecule composed of a glycosphingolipid (ceramide and oligosaccharide) with one or more sialic acids (e.g. n-acetylneuraminic acid, NANA) linked on the sugar chain. NeuNAc, an acetylated derivative of the carbohydrate sialic acid, makes the head groups of gangliosides anionic at pH 7, which distinguishes them from globosides.

As used herein, the term "ST8SIA1" also known as "Alpha-N-acetylneuraminide alpha-2,8-sialyltransferase" has its general meaning in this art and Catalyzes the addition of sialic acid in alpha 2,8-linkage to the sialic acid moiety of the ganglioside GM3 to form ganglioside GD3 (Uniprot accession number Q92185).

As used herein, the term "GD3" has its general meaning in this art and is defined by the chemical structure: aNeu5Ac (2-8)aNeu5Ac(2-3)bDGalp(1-4)bDG1cp(1-1)Cer. In some aspects, the GD3 is human GD3. In some aspects, the GD3 is rat GD3. In some aspects, the GD3 is mouse GD3. In some aspects, the GD3 is primate GD3. GD3 includes variants, isoforms, homologs, orthologs and paralogs of human ganglioside GD3.

As used herein, the term "biological sample" refers to any sample obtained from a subject, such as a serum sample, a plasma sample, a urine sample, a blood sample, a lymph sample, or a tissue biopsy. In a particular embodiment, the biological sample is a tissue biopsy.

As used herein, the term "tissue", when used in reference to a part of a body or of an organ, generally refers to an aggregation or collection of morphologically similar cells and associated accessory and support cells and intercellular matter, including extracellular matrix material, vascular supply, and fluids, acting together to perform specific functions in the body. There are generally four basic types of tissue in animals and humans including muscle, nerve, epithelial, and connective tissues.

As used herein, the term "cell" refers to the basic structural, functional, and biological unit of all known organisms. Cells are the smallest units of life, and hence are often referred to as the "building blocks of life". Cells consist of cytoplasm enclosed within a membrane, which contains many biomolecules such as proteins and nucleic acids. In some embodiment, the cell is selected from the following group but not limited to eukaryotic cell, mammary epithelial cells, keratinocytes, cardiac myocytes, chondrocytes, endothelial cells (large vessels), endothelial cells (microvascular), epithelial cells, fibroblasts, follicle dermal papilla cells, hepatocytes, melanocytes, osteoblasts, preadipocytes, cells of the immune system, skeletal muscle cells, smooth muscle cells, adipocytes, neurons, glial cells, contractile cells, exocrine secretory epithelial cells, extracellular matrix cells, hormone secreting cells, keratinizing epithelial cells, islet cells, lens cells, mesenchymal stem cells, pancreatic acinar cells, Paneth cells of the small intestine, cells of hemopoietic linage, cells of the nervous system, sense organ and peripheral neuron supporting cells and wet stratified barrier epithelial cells.

As used herein, the term "senescence" has its general mean in the art and refers to the permanent cessation of DNA replication and cell growth that is not reversible by growth factors. Senescence can be characterized by certain morphological features including, but not limited to, increased size, flattened morphology, increased granularity, and senescence-associated β-galactosidase activity (SA-β-gal).

As used herein, the term "senescent cell" is generally thought to be derived from a cell type that typically replicates, but as a result of aging or other event that causes a change in cell state, can no longer replicate. It remains metabolically active and commonly adopts a senescence associated secretory phenotype (SASP) that includes chemokines, cytokines and extracellular matrix and fibrosis modifying proteins and enzymes. The nucleus of senescent cells is often characterized by senescence-associated heterochromatin foci and DNA segments with chromatin alterations reinforcing senescence. Without implying any limitation on the practice of what is claimed in this disclosure that is not explicitly stated or required, the invention is premised on the hypothesis that senescent cells cause or mediate certain conditions associated with tissue damage or aging. For the purpose of practicing aspects of this invention, senescent cells can be identified as expressing at least one marker selected from p16, senescence-associated β-galactosidase, and lipofuscin; sometimes two or more of these markers, and other markers of SASP such a,s but not limited to, interleukin 6 (IL-6), and inflammatory, angiogenic and extracellular matrix modifying proteins.

As used herein, the term "senescent cell clearance" refers to a compound that selectively (preferentially or to a greater extent) destroys, kills, removes, or promotes selective destruction of senescent cells. , i.e., the compound destroys senescent cells in a biologically, clinically, and/or statistically significant manner as compared to its ability to destroy or kill non-senescent cells, or Annihilate. The senescent cell-depleting compound is sufficient to selectively kill established senescent cells, but is in an insufficient amount to kill non-senescent cells in a clinically or biologically significant manner.

As used herein, the term "senescence process" refers to a cellular response characterized by a stable growth arrest and other phenotypic alterations that include a proinflammatory secretome. Senescence plays roles in normal development, maintains tissue homeostasis, and limits tumor progression.

In some embodiment, the co-expression of GD3 with a senescence marker is suitable to use as a radiotracer.

As used herein, the term "radiotracer" has its general meaning in the art and refers to a chemical compound in which one or more atoms have been replaced by a radionuclide so by virtue of its radioactive decay it can be used to explore the mechanism of chemical reactions by tracing the path that the radioisotope follows from reactants to products.

In some embodiment, an anti GD3 radiotracer (radiolabelled antibody) would identify senescent cells in age-related diseases in order to better treat them.

As used herein, the term "senescence marker" has its general meaning in the art and refers to marker shown to be present in senescent cells only.

In some embodiment, the senescence marker is selected from the group consisting of but not limited to: SA-b-gal, $p16^{INK4a}$, Lamin B1, SASP, Telomere-Induced foci (TIFs) or p21

As used herein, the term "age-related disorder" or "age-related disease" or "senescent cells accumulation related disease" refers to disorders or diseases in which aging is a major risk factor. Based on the type of diseases, age-related diseases or disorders is selected from the following group but not limited to: aging or chronic age-related pathology (e.g arthritis or osteoarthritis, osteoporosis and atherosclerosis); dysplastic or preneoplastic lesions, benign prostatic hyperplasia; normal and/or tumor tissues following DNA-damaging therapy; Alzheimer's disease, Parkinson's disease, cataracts, macular degeneration, glaucoma, atherosclerosis, acute coronary syndrome, myocardial infarction, stroke, hypertension, pulmonary fibrosis, kidney fibrosis, idiopathic pulmonary fibrosis (IPF), chronic obstructive pulmonary disease (COPD), osteoarthritis, osteoporosis, type 2 diabetes, obesity, fat dysfunction, coronary artery disease, cerebrovascular disease, periodontal disease; cancer treatment-related disability (e.g.atrophy and fibrosis in various tissues), brain and heart injury, and therapy-related myelodysplastic syndromes; Hutchinson-Gilford progeria syndrome, Werner syndrome, Cockayne syndrome, exroderma pigmentosum, ataxia telangiectasia, Fanconi anemia, dyskeratosis congenital, aplastic anemia, idiopathic pulmonary fibrosis; cardiovascular diseases such as angina, aortic aneurysm, arrhythmia, brain aneurysm, cardiac diastolic dysfunction, cardiac fibrosis, cardiac stress resistance, cardiomyopathy, carotid artery disease, coronary thrombosis, endocarditis, hypercholesterolemia, hyperlipidemia, mitral valve prolapsed, and peripheral vascular disease; inflammatory or autoimmune diseases such as herniated intervertebral disc, inflammatory bowel disease, kyphosis, oral mucositis, lupus, interstital cystitis, scleroderma, and alopecia; neurodegenerative diseases such as dementia, Huntington's disease, motor neuron dysfunction, age-related memory decline, and depression/mood disorders; metabolic diseases such as diabetic ulcer and metabolic syndrome; pulmonary diseases such as age-related loss of pulmonary function, asthma, bronchiectasis, cystic fibrosis, emphysema, and age-associated sleep apnea; gastrointestinal diseases such as Barrett's esophagus; age-related disorders such as liver fibrosis, muscle fatigue, oral submucosa fibrosis, pancreatic fibrosis, benign prostatic hyperplasia (BPH), and age-related sleep disorders; reproductive disorders such as menopause (male and female), egg supply (female), sperm viability (male), fertility (male and female), sex drive, and erectile function and arousal (male and female); dermatological diseases such as atopic dermatitis, cutaneous lupus, cutaneous lymphomas, dysesthesia, eczema, eczematous eruptions, eosinophilic dermatosis, fibrohistocytic proliferations of skin, hyperpigmentation, immunobullous dermatosis, nevi, pemphigoid, pemphigus, pruritis, psoriasis, rashes, reactive neutrophilic dermatosis, rhytides, and urticarial; and other diseases such as diabetic wound healing, post-transplant kidney fibrosis, and carotid thrombosis. As used herein, the term "pulmonary cell senescence" refers to pulmonary cells such as pulmonary vascular endothelial cells, pulmonary artery smooth muscle cells, alveolar or branchial epithelial cells or lung fibroblasts which undergo a senescence process such as described above. Diseases involving pulmonary cell senescence are preferably selected from: Chronic obstructive pulmonary disease (COPD lung fibrosis, cystic fibrosis, chronic asthma, and potentially, any type of chronic lung disease, secondary pulmonary fibrosis after coronavirus infection (e.g. SARS-coronavirus such as SARS-CoV1 or SARS-CoV 2).

As used herein, the term "severe acute respiratory syndrome coronavirus" or "SARS-coronavirus" is a strain of virus that causes severe acute respiratory syndrome. It is an enveloped, positive-sense, single-stranded RNA virus which infects the epithelial cells within the lungs. The virus enters the host cell by binding to the ACE2 receptor. SARS-coronavirus comprises SARS-CoV 1 or SARS-CoV 2.

As used herein, the term "severe acute respiratory syndrome coronavirus 1" (SARS-CoV-1) is the coronavirus responsible for the SARS epidemic from 2002 to 2004. It is a strain of the coronavirus species SARSr-CoV. This infectious agent is said to have appeared in November 2002 in Guangdong province, China. Between Nov. 1, 2002 and Aug. 31, 2003, the virus would have infected 8,096 people in thirty countries, causing 774 deaths, mainly in China, Hong Kong, Taiwan, and Southeast Asia. It is a single-stranded RNA virus of positive polarity belonging to the genus *betacoronavirus*

As used herein, the term "severe acute respiratory syndrome coronavirus 2" (SARS-CoV-2) is a positive-sense single-stranded RNA virus. It causes coronavirus disease 2019 (COVID-19), a respiratory illness. SARS-CoV-2 is a member of the subgenus *Sarbecovirus* (beta-CoV lineage B). Its RNA sequence is approximately 30,000 bases in length. SARS-CoV-2 is unique among known betacoronaviruses in its incorporation of a polybasic cleavage site, a characteristic known to increase pathogenicity and transmissibility in other viruses.

In some embodiments, the patient had suffered from COVID-19.

In a particular embodiment, the senescent cells accumulation related disease is: pulmonary fibrosis; kidney fibrosis; arthritis; osteoporosis, or chronic obstructive pulmonary disease (COPD).

As used herein, the term "pulmonary diseases" or "pulmonary disorders" include, but are not limited to idiopathic pulmonary fibrosis (IPF), chronic obstructive pulmonary disease (COPD), asthma, cystic fibrosis, bronchiectasis, and emphysema.

As used herein, the term "COPD" refers a lung disease defined by persistently poor airflow resulting from the breakdown of lung tissue, emphysema, and the dysfunction of the small airways, obstructive bronchiolitis. Primary symptoms of COPD include shortness of breath, wheezing, chest tightness, chronic cough, and excess sputum production. Elastase from cigarette smoke-activated neutrophils and macrophages can disintegrate the extracellular matrix of alveolar structures, resulting in enlarged air spaces and loss of respiratory capacity. COPD can be caused by, for example, tobacco smoke, cigarette smoke, cigar smoke, secondhand smoke, pipe smoke, occupational exposure, exposure to dust, smoke, fumes, and pollution, occurring over decades thereby implicating aging as a risk factor for developing COPD.

The processes involved in causing lung damage can include, for example, oxidative stress produced by the high concentrations of free radicals in tobacco smoke, cytokine release due to the inflammatory response to irritants in the airway, and impairment of anti-protease enzymes by tobacco smoke and free radicals, allowing proteases to damage the lungs. Genetic susceptibility can also contribute to the disease. In about 1% percent of people with COPD, the disease results from a genetic disorder that causes low level production of alpha-1-antitrypsin in the liver. Alpha-1-antitrypsin is normally secreted into the bloodstream to help protect the lungs.

Pulmonary fibrosis is a chronic and progressive lung disease characterized by stiffening and scarring of the lung, which can lead to respiratory failure, lung cancer, and heart failure. Fibrosis is associated with repair of epithelium. Fibroblasts are activated, production of extracellular matrix proteins is increased, and trans differentiation to contractile myofibroblasts contribute to wound contraction. A provisional matrix plugs the injured epithelium and provides a scaffold for epithelial cell migration, involving an epithelial-mesenchymal transition (EMT). Blood loss associated with epithelial injury induces platelet activation, production of growth factors, and an acute inflammatory response. Normally, the epithelial barrier heals and the inflammatory response resolves. However, in fibrotic disease the fibroblast response continues, resulting in unresolved wound healing. Formation of fibroblastic foci is a feature of the disease, reflecting locations of ongoing fibrogenesis.

Subjects at risk of developing pulmonary fibrosis include, for example, those exposed to environmental or occupational pollutants, such as asbestosis and silicosis; those who smoke cigarettes; those who have a connective tissue diseases such as RA, SLE, scleroderma, sarcoidosis, or Wegener's granulomatosis; those who have infections; those who take certain medications, including, for example, adriamycin, amiodarone, bleomycin, busufan, methotrexate, and nitrofurantoin; those subject to radiation therapy to the chest; and those whose family member have pulmonary fibrosis.

In some embodiment, adriamycin and bleomycin are used as an inducer of senescence and they are a cytotoxic agent that will induce DNA breaks. Indeed, Adriamycin induces DNA breaks which will activate the p53 pathway and thus the onset of senescence Symptoms of COPD can include any one of shortness of breath, wheezing, chest tightness, having to clear one's throat first thing in the morning because of excess mucus in the lungs, a chronic cough that produces sputum that can be clear, white, yellow or greenish, cyanosis, frequent respiratory infections, lack of energy, and unintended weight loss. Subjects with COPD can also experience exacerbations, during which symptoms worsen and persist for days or longer. Symptoms of pulmonary fibrosis include, for example, shortness of breath, particularly during exercise; dry, hacking cough; fast, shallow breathing; gradual, unintended weight loss; fatigue; aching joints and muscles; and clubbing of the fingers or toes.

As used, the term "polypathology" refers to an accumulation of pathologies that is to say when people suffer from at least two diseases, three disease, four diseases, five diseases or more than five diseases.

In a particular embodiment, the present invention relates to the prevention of cancer, in particular in the case where the patients will trigger pulmonary cancers secondary to their fibrosis.

As used herein, the term "prevention" relates to the set of actions, attitudes and behaviors which tend to avoid the occurrence of diseases or injuries or to maintain and improve health.

As used herein, the term "expression level" refers to the expression level of GD3 and may be determined by any technology known by a person skilled in the art. In particular, each gene expression level may be measured at the genomic and/or nucleic and/or protein level. In a particular embodiment, the expression level of gene is determined by measuring the amount of nucleic acid transcripts of each gene. In another embodiment, the expression level is determined by measuring the amount of each gene corresponding protein. The amount of nucleic acid transcripts can be measured by any technology known by a man skilled in the art.

As used herein, the term "co-expression level" refers to the expression level of GD3 with a senescence marker in a biological sample.

In particular, the measure may be carried out directly on an extracted messenger RNA (mRNA) sample, or on retrotranscribed complementary DNA (cDNA) prepared from extracted mRNA by technologies well-known in the art. Typically, the expression level of a gene is determined by determining the quantity of mRNA. For example the nucleic acid contained in the samples (e.g., cell or tissue prepared from the subject) is first extracted according to standard methods, for example using lytic enzymes or chemical solutions or extracted by nucleic-acid-binding resins following the manufacturer's instructions. The extracted mRNA is then detected by hybridization (e. g., Northern blot analysis, in situ hybridization) and/or amplification (e.g., RT-PCR). Other methods of Amplification include ligase chain reaction (LCR), transcription-mediated amplification (TMA), strand displacement amplification (SDA) and nucleic acid sequence based amplification (NASBA).

Nucleic acids having at least 10 nucleotides and exhibiting sequence complementarity or homology to the mRNA of interest herein find utility as hybridization probes or amplification primers. It is understood that such nucleic acids need not be identical, but are typically at least about 80% identical to the homologous region of comparable size, more preferably 85% identical and even more preferably 90-95% identical. In some embodiments, it will be advantageous to use nucleic acids in combination with appropriate means, such as a detectable label, for detecting hybridization.

Typically, the nucleic acid probes include one or more labels, for example to permit detection of a target nucleic acid molecule using the disclosed probes. In various applications, such as in situ hybridization procedures, a nucleic acid probe includes a label (e.g., a detectable label). A "detectable label" is a molecule or material that can be used to produce a detectable signal that indicates the presence or concentration of the probe (particularly the bound or hybridized probe) in a sample. Thus, a labelled nucleic acid molecule provides an indicator of the presence or concentration of a target nucleic acid sequence (e.g., genomic target nucleic acid sequence) (to which the labelled uniquely specific nucleic acid molecule is bound or hybridized) in a sample. A label associated with one or more nucleic acid molecules (such as a probe generated by the disclosed methods) can be detected either directly or indirectly. A label can be detected by any known or yet to be discovered mechanism including absorption, emission and/or scattering of a photon (including radio frequency, microwave frequency, infrared frequency, visible frequency and ultraviolet frequency photons). Detectable labels include colored, fluorescent, phosphorescent and luminescent molecules and materials, catalysts (such as enzymes) that convert one substance into another substance to provide a detectable difference (such as by converting a colorless substance into a colored substance or vice versa, or by producing a precipitate or increasing sample turbidity), haptens that can be detected by antibody binding interactions, and paramagnetic and magnetic molecules or materials.

Particular examples of detectable labels include fluorescent molecules (or fluorochromes). Numerous fluorochromes are known to those of skill in the art, and can be selected, for example from Life Technologies (formerly Invitrogen), e.g., see, The Handbook—A Guide to Fluorescent Probes and Labeling Technologies). Examples of particular fluorophores that can be attached (for example, chemically conjugated) to a nucleic acid molecule (such as a uniquely specific binding region) are provided in U.S. Pat. No. 5,866, 366 to Nazarenko et al., such as 4-acetamido-4'-isothiocyanatostilbene-2,2' disulfonic acid, acridine and derivatives such as acridine and acridine isothiocyanate, 5-(2'-aminoethyl) aminonaphthalene-l-sulfonic acid (EDANS), 4-amino-N-[3vinylsulfonyl)phenyl]naphthalimide-3,5 disulfonate (Lucifer Yellow VS), N-(4-anilino-1-naphthyl)maleimide, antllranilamide, Brilliant Yellow, coumarin and derivatives such as coumarin, 7-amino-4-methylcoumarin (AMC, Coumarin 120), 7-amino-4-trifluoromethylcouluarin (Coumarin 151); cyanosine; 4',6-diarninidino-2-phenylindole (DAPI); 5',5"dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulforlic acid; 5-[dimethylamino]naphthalene-1-sulfonyl chloride (DNS, dansyl chloride); 4-(4'-dimethylaminophenylazo)benzoic acid (DABCYL); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4, 6dicl1lorotriazin-2-yDarninofluorescein (DTAF), 2'7'dimethoxy-4'5'-dichloro-6-carboxyfluorescein (JOE), fluorescein, fluorescein isothiocyanate (FITC), and QFITC Q(RITC); 2',7'-difluorofluorescein (OREGON GREEN®); fluorescamine; IR144; IR1446; Malachite Green isothiocyanate; 4-methylumbelliferone; ortho cresolphthalein; nitrotyrosine; pararosaniline; Phenol Red; B-phycoerythrin; o-phthaldialdehyde; pyrene and derivatives such as pyrene, pyrene butyrate and succinimidyl 1-pyrene butyrate; Reactive Red 4 (Cibacron Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, rhodamine green, sulforhodamine B, sulforhodamine 101 and sulfonyl chloride derivative of sulforhodamine 101 (Texas Red); N,N,N',N'-tetramethyl-6-carboxyrhodamine (TAMRA); tetramethyl rhodamine; tetramethyl rhodamine isothiocyanate (TRITC); riboflavin; rosolic acid and terbium chelate derivatives. Other suitable fluorophores include thiol-reactive europium chelates which emit at approximately 617 mn (Heyduk and Heyduk, Analyt. Biochem. 248:216-27, 1997; J. Biol. Chem. 274:3315-22, 1999), as well as GFP, Lissamine™, diethylaminocoumarin, fluorescein chlorotriazinyl, naphthofluorescein, 4,7-dichlororhodamine and xanthene (as described in U.S. Pat. No. 5,800,996 to Lee et al.) and derivatives thereof. Other fluorophores known to those skilled in the art can also be used, for example those available from Life Technologies (Invitrogen; Molecular Probes (Eugene, Oreg.)) and including the ALEXA FLUOR® series of dyes (for example, as described in U.S. Pat. Nos. 5,696,157, 6,130,101 and 6,716, 979), the BODIPY series of dyes (dipyrrometheneboron difluoride dyes, for example as described in U.S. Pat. Nos. 4,774,339, 5,187,288, 5,248,782, 5,274,113, 5,338,854, 5,451,663 and 5,433,896), Cascade Blue (an amine reactive derivative of the sulfonated pyrene described in U.S. Pat. No. 5,132,432) and Marina Blue (U.S. Pat. No. 5,830,912).

In addition to the fluorochromes described above, a fluorescent label can be a fluorescent nanoparticle, such as a semiconductor nanocrystal, e.g., a QUANTUM DOT™ (obtained, for example, from Life Technologies (QuantumDot Corp, Invitrogen Nanocrystal Technologies, Eugene, Oreg.); see also, U.S. Pat. Nos. 6,815,064; 6,682,596; and 6,649, 138). Semiconductor nanocrystals are microscopic particles having size-dependent optical and/or electrical properties. When semiconductor nanocrystals are illuminated with a primary energy source, a secondary emission of energy occurs of a frequency that corresponds to the handgap of the semiconductor material used in the semiconductor nanocrystal. This emission can he detected as colored light of a specific wavelength or fluorescence. Semiconductor nanocrystals with different spectral characteristics are described in e.g., U.S. Pat. No. 6,602,671. Semiconductor nanocrystals that can he coupled to a variety of biological molecules (including dNTPs and/or nucleic acids) or substrates by techniques described in, for example, Bruchez et al., Science 281 :20132016, 1998; Chan et al., Science 281:2016-2018, 1998; and U.S. Pat. No. 6,274,323. Formation of semiconductor nanocrystals of various compositions are disclosed in, e.g., U.S. Pat. Nos. 6,927, 069; 6,914,256; 6,855,202; 6,709,929; 6,689,338; 6,500,622; 6,306,736; 6,225,198; 6,207,392; 6,114,038; 6,048,616; 5,990,479; 5,690,807; 5,571,018; 5,505,928; 5,262,357 and in U.S. Patent Publication No. 2003/0165951 as well as PCT Publication No. 99/26299 (published May 27, 1999). Separate populations of semiconductor nanocrystals can he produced that are identifiable based on their different spectral characteristics. For example, semiconductor nanocrystals can he produced that emit light of different colors based on their composition, size or size and composition. For example, quantum dots that emit light at different wavelengths based on size (565 mn, 655 mn, 705 mn, or 800 mn emission wavelengths), which are suitable as fluorescent labels in the probes disclosed herein are available from Life Technologies (Carlshad, Calif.).

Additional labels include, for example, radioisotopes (such as $^{3}H$), metal chelates such as DOTA and DPTA chelates of radioactive or paramagnetic metal ions like Gd3+, and liposomes.

Detectable labels that can he used with nucleic acid molecules also include enzymes, for example horseradish peroxidase, alkaline phosphatase, acid phosphatase, glucose oxidase, beta-galactosidase, beta-glucuronidase, or beta-lactamase.

Alternatively, an enzyme can be used in a metallographic detection scheme. For example, silver in situ hybridization (SISH) procedures involve metallographic detection schemes for identification and localization of a hybridized genomic target nucleic acid sequence. Metallographic detection methods include using an enzyme, such as alkaline phosphatase, in combination with a water-soluble metal ion and a redox-inactive substrate of the enzyme. The substrate is converted to a redox-active agent by the enzyme, and the redoxactive agent reduces the metal ion, causing it to form a detectable precipitate. (See, for example, U.S. Patent Application Publication No. 2005/0100976, PCT Publication No. 2005/003777 and U.S. Patent Application Publication No. 2004/0265922). Metallographic detection methods also include using an oxido-reductase enzyme (such as horseradish peroxidase) along with a water soluble metal ion, an oxidizing agent and a reducing agent, again to form a detectable precipitate. (See, for example, U.S. Pat. No. 6,670,113).

Probes made using the disclosed methods can be used for nucleic acid detection, such as ISH procedures (for example, fluorescence in situ hybridization (FISH), chromogenic in situ hybridization (CISH) and silver in situ hybridization (SISH)) or comparative genomic hybridization (CGH).

In situ hybridization (ISH) involves contacting a sample containing target nucleic acid sequence (e.g., genomic target nucleic acid sequence) in the context of a metaphase or interphase chromosome preparation (such as a cell or tissue sample mounted on a slide) with a labelled probe specifically hybridizable or specific for the target nucleic acid sequence (e.g., genomic target nucleic acid sequence). The slides are optionally pre-treated, e.g., to remove paraffin or other materials that can interfere with uniform hybridization. The sample and the probe are both treated, for example by heating to denature the double stranded nucleic acids. The probe (formulated in a suitable hybridization buffer) and the sample are combined, under conditions and for sufficient time to permit hybridization to occur (typically to reach equilibrium). The chromosome preparation is washed to remove excess probe, and detection of specific labeling of the chromosome target is performed using standard techniques.

For example, a biotinylated probe can be detected using fluorescein-labelled avidin or avidin-alkaline phosphatase. For fluorochrome detection, the fluorochrome can be detected directly, or the samples can be incubated, for example, with fluorescein isothiocyanate (FITC)-conjugated avidin. Amplification of the FITC signal can be effected, if necessary, by incubation with biotin-conjugated goat anti-avidin antibodies, washing and a second incubation with FITC-conjugated avidin. For detection by enzyme activity, samples can be incubated, for example, with streptavidin, washed, incubated with biotin-conjugated alkaline phosphatase, washed again and pre-equilibrated (e.g., in alkaline phosphatase (AP) buffer). For a general description of in situ hybridization procedures, see, e.g., U.S. Pat. No. 4,888,278.

Numerous procedures for FISH, CISH, and SISH are known in the art. For example, procedures for performing FISH are described in U.S. Pat. Nos. 5,447,841; 5,472,842; and 5,427,932; and for example, in Pirlkel et al., Proc. Natl. Acad. Sci. 83:2934-2938, 1986; Pinkel et al., Proc. Natl. Acad. Sci. 85:9138-9142, 1988; and Lichter et al., Proc. Natl. Acad. Sci. 85:9664-9668, 1988. CISH is described in, e.g., Tanner et al., Am. .1. Pathol. 157:1467-1472, 2000 and U.S. Pat. No. 6,942,970. Additional detection methods are provided in U.S. Pat. No. 6,280,929.

Numerous reagents and detection schemes can be employed in conjunction with FISH, CISH, and SISH procedures to improve sensitivity, resolution, or other desirable properties. As discussed above probes labelled with fluorophores (including fluorescent dyes and QUANTUM DOTS®) can be directly optically detected when performing FISH. Alternatively, the probe can be labelled with a non-fluorescent molecule, such as a hapten (such as the following non-limiting examples: biotin, digoxigenin, DNP, and various oxazoles, pyrrazoles, thiazoles, nitroaryls, benzofurazans, triterpenes, ureas, thioureas, rotenones, coumarin, courmarin-based compounds, Podophyllotoxin, Podophyllotoxin-based compounds, and combinations thereof), ligand or other indirectly detectable moiety. Probes labeled with such non-fluorescent molecules (and the target nucleic acid sequences to which they bind) can then be detected by contacting the sample (e.g., the cell or tissue sample to which the probe is bound) with a labelled detection reagent, such as an antibody (or receptor, or other specific binding partner) specific for the chosen hapten or ligand. The detection reagent can be labelled with a fluorophore (e.g., QUANTUM DOT®) or with another indirectly detectable moiety, or can be contacted with one or more additional specific binding agents (e.g., secondary or specific antibodies), which can be labelled with a fluorophore.

In other examples, the probe, or specific binding agent (such as an antibody, e.g., a primary antibody, receptor or other binding agent) is labelled with an enzyme that is capable of converting a fluorogenic or chromogenic composition into a detectable fluorescent, colored or otherwise detectable signal (e.g., as in deposition of detectable metal particles in SISH). As indicated above, the enzyme can be attached directly or indirectly via a linker to the relevant probe or detection reagent. Examples of suitable reagents (e.g., binding reagents) and chemistries (e.g., linker and attachment chemistries) are described in U.S. Patent Application Publication Nos. 2006/0246524; 2006/0246523, and 2007/0117153.

It will be appreciated by those of skill in the art that by appropriately selecting labelled probe-specific binding agent pairs, multiplex detection schemes can he produced to facilitate detection of multiple target nucleic acid sequences (e.g., genomic target nucleic acid sequences) in a single assay (e.g., on a single cell or tissue sample or on more than one cell or tissue sample). For example, a first probe that corresponds to a first target sequence can he labelled with a first hapten, such as biotin, while a second probe that corresponds to a second target sequence can be labelled with a second hapten, such as DNP. Following exposure of the sample to the probes, the bound probes can he detected by contacting the sample with a first specific binding agent (in this case avidin labelled with a first fluorophore, for example, a first spectrally distinct QUANTUM DOT®, e.g., that emits at 585 mn) and a second specific binding agent (in this case an anti-DNP antibody, or antibody fragment, labelled with a second fluorophore (for example, a second spectrally distinct QUANTUM DOT®, e.g., that emits at 705 mn). Additional probes/binding agent pairs can he added to the multiplex detection scheme using other spectrally distinct fluorophores. Numerous variations of direct, and indirect (one step, two step or more) can he envisioned, all of which are suitable in the context of the disclosed probes and assays.

Probes typically comprise single-stranded nucleic acids of between 10 to 1000 nucleotides in length, for instance of between 10 and 800, more preferably of between 15 and 700, typically of between 20 and 500. Primers typically are shorter single-stranded nucleic acids, of between 10 to 25 nucleotides in length, designed to perfectly or almost perfectly match a nucleic acid of interest, to be amplified. The probes and primers are "specific" to the nucleic acids they hybridize to, i.e. they preferably hybridize under high stringency hybridization conditions (corresponding to the highest melting temperature Tm, e.g., 50% formamide, 5× or 6×SCC. SCC is a 0.15 M NaCl, 0.015 M Na-citrate).

The nucleic acid primers or probes used in the above amplification and detection method may be assembled as a kit. Such a kit includes consensus primers and molecular probes. A preferred kit also includes the components necessary to determine if amplification has occurred. The kit may also include, for example, PCR buffers and enzymes; positive control sequences, reaction control primers; and instructions for amplifying and detecting the specific sequences.

In some embodiments, the methods of the invention comprise the steps of providing total RNAs extracted from cumulus cells and subjecting the RNAs to amplification and hybridization to specific probes, more particularly by means of a quantitative or semi-quantitative RT-PCR.

In some embodiments, the level is determined by DNA chip analysis. Such DNA chip or nucleic acid microarray consists of different nucleic acid probes that are chemically attached to a substrate, which can be a microchip, a glass slide or a microsphere-sized bead. A microchip may be constituted of polymers, plastics, resins, polysaccharides, silica or silica-based materials, carbon, metals, inorganic glasses, or nitrocellulose. Probes comprise nucleic acids such as cDNAs or oligonucleotides that may be about 10 to about 60 base pairs. To determine the level, a sample from a test subject, optionally first subjected to a reverse transcription, is labelled and contacted with the microarray in hybridization conditions, leading to the formation of complexes between target nucleic acids that are complementary to probe sequences attached to the microarray surface. The labelled hybridized complexes are then detected and can be quantified or semi-quantified. Labelling may be achieved by various methods, e.g. by using radioactive or fluorescent labelling. Many variants of the microarray hybridization technology are available to the man skilled in the art (see e.g. the review by Hoheisel, Nature Reviews, Genetics, 2006, 7:200-210).

In some embodiments, the nCounter® Analysis system is used to detect intrinsic gene expression. The basis of the nCounter® Analysis system is the unique code assigned to each nucleic acid target to be assayed (International Patent Application Publication No. WO 08/124847, U.S. Pat. No. 8,415,102 and Geiss et al. Nature Biotechnology. 2008. 26(3): 317-325; the contents of which are each incorporated herein by reference in their entireties). The code is composed of an ordered series of colored fluorescent spots which create a unique barcode for each target to be assayed. A pair of probes is designed for each DNA or RNA target, a biotinylated capture probe and a reporter probe carrying the fluorescent barcode. This system is also referred to, herein, as the nanoreporter code system. Specific reporter and capture probes are synthesized for each target. The reporter probe can comprise at a least a first label attachment region to which are attached one or more label monomers that emit light constituting a first signal; at least a second label attachment region, which is non-over-lapping with the first label attachment region, to which are attached one or more label monomers that emit light constituting a second signal;

and a first target- specific sequence. Preferably, each sequence specific reporter probe comprises a target specific sequence capable of hybridizing to no more than one gene and optionally comprises at least three, or at least four label attachment regions, said attachment regions comprising one or more label monomers that emit light, constituting at least a third signal, or at least a fourth signal, respectively. The capture probe can comprise a second target-specific sequence; and a first affinity tag. In some embodiments, the capture probe can also comprise one or more label attachment regions. Preferably, the first target-specific sequence of the reporter probe and the second target- specific sequence of the capture probe hybridize to different regions of the same gene to be detected. Reporter and capture probes are all pooled into a single hybridization mixture, the "probe library". The relative abundance of each target is measured in a single multiplexed hybridization reaction. The method comprises contacting the tumor tissue sample with a probe library, such that the presence of the target in the sample creates a probe pair-target complex. The complex is then purified. More specifically, the sample is combined with the probe library, and hybridization occurs in solution. After hybridization, the tripartite hybridized complexes (probe pairs and target) are purified in a two-step procedure using magnetic beads linked to oligonucleotides complementary to universal sequences present on the capture and reporter probes. This dual purification process allows the hybridization reaction to be driven to completion with a large excess of target-specific probes, as they are ultimately removed, and, thus, do not interfere with binding and imaging of the sample. All post hybridization steps are handled robotically on a custom liquid-handling robot (Prep Station, NanoString Technologies). Purified reactions are typically deposited by the Prep Station into individual flow cells of a sample cartridge, bound to a streptavidin-coated surface via the capture probe, electrophoresed to elongate the reporter probes, and immobilized. After processing, the sample cartridge is transferred to a fully automated imaging and data collection device (Digital Analyzer, NanoString Technologies). The level of a target is measured by imaging each sample and counting the number of times the code for that target is detected. For each sample, typically 600 fields-of-view (FOV) are imaged (1376×1024 pixels) representing approximately 10 mm2 of the binding surface. Typical imaging density is 100-1200 counted reporters per field of view depending on the degree of multiplexing, the amount of sample input, and overall target abundance. Data is output in simple spreadsheet format listing the number of counts per target, per sample. This system can be used along with nanoreporters. Additional disclosure regarding nanoreporters can be found in International Publication No. WO 07/076129 and WO07/076132, and US Patent Publication No. 2010/0015607 and 2010/0261026, the contents of which are incorporated herein in their entireties. Further, the term nucleic acid probes and nanoreporters can include the rationally designed (e.g. synthetic sequences) described in International Publication No. WO 2010/019826 and US Patent Publication No.2010/0047924, incorporated herein by reference in its entirety.

Method of Treatment

In a second embodiment, the present invention relates to a method for treating senescent cells accumulation related disease in a subject in need thereof, comprising administering to said subject a therapeutically effective amount of a GD3 inhibitor.

In some embodiment, the present invention relates to the treatment of age-related anti-polypathologies in a subject in need thereof, comprising administering to said subject a therapeutically effective amount of a GD3 inhibitor.

The present invention also relates to a method for diagnosing and treating senescent cells accumulation related disease in a subject in need thereof comprising i) detecting the co-expression of ST8Sia1 (GD3) with a senescence marker in a biological sample obtained from a subject, ii) concluding that the subject suffers from a senescent cells accumulation related disease when the co-expression of GD3 with senescence marker is detected in the biological sample and iii) treating the said subject with a GD3 inhibitor.

The present invention also relates to a method for identifying whether a cell is in senescence process comprising the steps of: i) measuring the co-expression level of ST8Sia1 (GD3) with a senescence marker in a biological sample; ii) comparing the co-expression level measured at step i) with its predetermined reference value, iii) concluding that the cell is in senescence process when the co-expression level of GD3 with a senescence marker is higher than its predetermined reference value, iv) administering a GD3 inhibitor.

As used herein, the terms "subject" or "patient" denote a mammal, such as a rodent, a feline, a canine, and a primate. Particularly, the subject according to the invention is a human. Particularly, the subject according to the invention is a child, a teenager, an adult or an elderly persons. In some embodiments, the subject is more than 15 years old. In some embodiments, the subject is more than 20 years old. In some embodiments, the subject is more than 25 years old. In some embodiments, the subject is more than 30 years old. In some embodiments, the subject is more than 35 years old.

As used herein, the term "inhibitor" as used herein includes not only drugs for inhibiting activity of target molecules, but also drugs for inhibiting the expression of target molecules.

As used herein, the term "GD3 inhibitor" has its general meaning in the art and refers to an inhibitor of GD3. The inhibitor of GD3 include but are not limited to GD3 antibody, CAR-T cell, CAR NK cell.

In some embodiment, the present invention relates to senotherapy strategy including any type of targeting (e.g. antibody, drug, CAR T, CAR NK . . . ) of GD3 that aimed at blocking with with senomorphic agent or eliminating with senolytic agent senescent cells by targeting GD3.

In a particular embodiment, the GD3 inhibitor is a CAR-T cell.

As used herein the term "CAR-T cell" refers to a T lymphocyte that has been genetically engineered to express a CAR. The definition of CAR T-cells encompasses all classes and subclasses of T-lymphocytes including CD4+, CD8+ T cells, gamma delta T cells as well as effector T cells, memory T cells, regulatory T cells, and the like. The T lymphocytes that are genetically modified may be "derived" or "obtained" from the subject who will receive the treatment using the genetically modified T cells or they may "derived" or "obtained" from a different subject. As used herein, the term "Chimeric Antigen Receptor" or alternatively a "CAR" refers to a set of polypeptides, typically two in the simplest embodiments, which when in an immune effector cell, provides the cell with specificity for a target cell, typically a cancer cell, and with intracellular signal generation. In some embodiments, a CAR comprises at least an extracellular antigen binding domain, a transmembrane domain and a cytoplasmic signaling domain (also referred to herein as "an intracellular signaling domain") comprising a functional signaling domain derived from a stimulatory molecule and/or costimulatory molecule as defined below. In some aspects, the set of polypeptides are contiguous with each other. In some embodiments, the set of polypeptides include a dimerization switch that, upon the presence of a dimerization molecule, can couple the polypeptides to one another, e.g., can couple an antigen binding domain to an intracellular signaling domain. In some embodiments, the stimulatory molecule is the zeta chain associated with the T cell receptor complex. In some embodiments, the cytoplasmic signaling domain further comprises one or more functional signaling domains derived from at least one costimulatory molecule as defined below. In some embodiments, the costimulatory molecule is chosen from the costimulatory molecules described herein, e.g., 4-1BB (i.e., CD137), CD27 and/or CD28. In some embodiments, the CAR comprises a chimeric fusion protein comprising an extracellular antigen binding domain, a transmembrane domain and an intracellular signaling domain comprising a functional signaling domain derived from a stimulatory molecule. In some embodiments, the CAR comprises a chimeric fusion protein comprising an extracellular antigen binding domain, a transmembrane domain and an intracellular signaling domain comprising a functional signaling domain derived from a costimulatory molecule and a functional signaling domain derived from a stimulatory molecule. In some embodiments, the CAR comprises a chimeric fusion protein comprising an extracellular antigen binding domain, a transmembrane domain and an intracellular signaling domain comprising two functional signaling domains derived from one or more costimulatory molecule(s) and a functional signaling domain derived from a stimulatory molecule. In some embodiments, the CAR comprises a chimeric fusion protein comprising an extracellular antigen binding domain, a transmembrane domain and an intracellular signaling domain comprising at least two functional signaling domains derived from one or more costimulatory molecule(s) and a functional signaling domain derived from a stimulatory molecule. In some embodiments, the CAR comprises an optional leader sequence at the amino-terminus (N-ter) of the CAR fusion protein. In some embodiments, the CAR further comprises a leader sequence at the N-terminus of the extracellular antigen binding domain, wherein the leader sequence is optionally cleaved from the antigen binding domain (e.g., a scFv) during cellular processing and localization of the CAR to the cellular membrane. In particular aspects, CARs comprise fusions of single-chain variable fragments (scFv) derived from monoclonal antibodies, fused to CD3-zeta a transmembrane domain and endodomain. In some embodiments, CARs comprise domains for additional co-stimulatory signaling, such as CD3-zeta, FcR, CD27, CD28, CD137, DAPIO, and/or 0X40. In some embodiments, molecules can be co-expressed with the CAR, including co-stimulatory molecules, reporter genes for imaging (e.g., for positron emission tomography), gene products that conditionally ablate the T cells upon addition of a pro-drug, homing receptors, chemokines, chemokine receptors, cytokines, and cytokine receptors.

In a particular embodiment, the GD3 inhibitor is a CAR NK cell. As used herein the term "CAR-NK" refers to natural killer (NK) cells that has been genetically engineered to express a CAR. NK cells are defined as CD56+ and CD3− cells and are subdivided into cytotoxic and immunoregulatory. They are of great clinical interest because they contribute to the graft-vs-leukemia/graft-vs-tumor effect but are not responsible for graft-vs-host disease. NK cells can be generated from various sources such as umbilical cord blood, bone marrow, human embryonic stem cells, and induced pluripotent stem cells. However, tumors can escape the cytotoxicity of NK cells when they are directed against NKG2D ligands MICA and MICB (major histocompatibility complex class I chain-related protein A/B). Henceforth, preclinical research has been reported for CAR-modified primary human NK cells redirected against CD19, CD20, CD244, and HER2, as well as CAR-expressing NK-92 cells targeted to a wider range of cancer antigens. Primary NK cells engineered to express CARs have potential benefits compared to CAR-T cells. NK cells have spontaneous cytotoxic activity and can generate target cell death independent of tumor antigen, while T lymphocytes only kill their targets by a CAR-specific mechanism. Therefore, in the setting of antigen downregulation by tumor cells attempting to escape immune detection, NK cells would still be effective against tumor cells. In addition, primary human NK cells produce cytokines, such as interferon gamma, interleukin 3, and granulocyte-macrophage colony-stimulating factor, that differ from the proinflammatory cytokines produced by T cells that are responsible for the onset of cytokine release syndrome. Individual NK cells can survive after contacting and killing multiple target cells, possibly reducing the number of cells that need to be adoptively transferred (ie, the ex vivo stimulation and expansion of autologous or allogeneic lymphocytes, followed by reinfusion of the expanded lymphocyte population into the patient, in contrast to T cells). Furthermore, whereas the long-term persistence of CAR-T cells may maintain on-target, off-tumor toxicity such as the B cell aplasia seen with anti-CD19 CAR-T cells, mature NK cells are short lived and are expected to disappear after facilitating their anticancer effects In a particular embodiment, the GD3 inhibitor is a peptide, petptidomimetic, small organic molecule, antibody, aptamers, siRNA or antisense oligonucleotide. The term "peptidomimetic" refers to a small protein-like chain designed to mimic a peptide.

In a particular embodiment, the GD3 inhibitor is an aptamer. Aptamers are a class of molecule that represents an alternative to antibodies in term of molecular recognition. Aptamers are oligonucleotide or oligopeptide sequences with the capacity to recognize virtually any class of target molecules with high affinity and specificity.

In a particular embodiment, the GD3 inhibitor is a small organic molecule. The term "small organic molecule" refers to a molecule of a size comparable to those organic molecules generally used in pharmaceuticals. The term excludes biological macromolecules (e.g., proteins, nucleic acids, etc.). Preferred small organic molecules range in size up to about 5000 Da, more preferably up to 2000 Da, and most preferably up to about 1000 Da.

In some embodiments, the GD3 inhibitor is an antibody. As used herein, the term "antibody" is used in the broadest sense and specifically covers monoclonal antibodies, polyclonal antibodies, multi-specific antibodies (e.g. bispecific antibodies) formed from at least two intact antibodies, and antibody fragments so long as they exhibit the desired biological activity. The term includes antibody fragments that comprise an antigen binding domain such as Fab', Fab, F(ab')2, single domain antibodies (DABs), TandAbs dimer, Fv, scFv (single chain Fv), dsFv, ds-scFv, Fd, linear antibodies, minibodies, diabodies, bispecific antibody fragments, bibody, tribody (scFv-Fab fusions, bispecific or trispecific, respectively); sc-diabody; kappa(lamda) bodies (scFv-CL fusions); BiTE (Bispecific T-cell Engager, scFv-scFv tandems to attract T cells); DVD-Ig (dual variable domain antibody, bispecific format); SIP (small immunoprotein, a kind of minibody); SMIP ("small modular immunopharmaceutical" scFv-Fc dimer; DART (ds-stabilized diabody "Dual Affinity ReTargeting"); small antibody mimetics comprising one or more CDRs and the like. The techniques for preparing and using various antibody-based constructs and fragments are well known in the art (see Kabat et al., 1991, specifically incorporated herein by reference). Diabodies, in particular, are further described in EP 404,097 and WO 93/11161; whereas linear antibodies are further described in Zapata et al. (1995). Antibodies can be fragmented using conventional techniques. For example, F(ab')2 fragments can be generated by treating the antibody with pepsin. The resulting F(ab')2 fragment can be treated to reduce disulfide bridges to produce Fab' fragments. Papain digestion can lead to the formation of Fab fragments. Fab, Fab' and F(ab')2, scFv, Fv, dsFv, Fd, dAbs, TandAbs, ds-scFv, dimers, minibodies, diabodies, bispecific antibody fragments and other fragments can also be synthesized by recombinant techniques or can be chemically synthesized. Techniques for producing antibody fragments are well known and described in the art. For example, each of Beckman et al., 2006; Holliger & Hudson, 2005; Le Gall et al., 2004; Reff & Heard, 2001 ; Reiter et al., 1996; and Young et al., 1995 further describe and enable the production of effective antibody fragments. In some embodiments, the antibody is a "chimeric" antibody as described in U.S. Pat. No. 4,816,567. In some embodiments, the antibody is a humanized antibody, such as described U.S. Pat. Nos. 6,982,321 and 7,087,409. In some embodiments, the antibody is a human antibody. A "human antibody" such as described in U.S. Pat. Nos. 6,075,181 and 6,150,584. In some embodiments, the antibody is a single domain antibody such as described in EP 0 368 684, WO 06/030220 and WO 06/003388. In a particular embodiment, the inhibitor is a monoclonal antibody. Monoclonal antibodies can be prepared and isolated using any technique that provides for the production of antibody molecules by continuous cell lines in culture. Techniques for production and isolation include but are not limited to the hybridoma technique, the human B-cell hybridoma technique and the EBV-hybridoma technique. In a particular embodiment, the antibody is specific of the isoform B of GD3. In some embodiments, the antibody is a single domain antibody. The term "single domain antibody" (sdAb) or "VHH" refers to the single heavy chain variable domain of antibodies of the type that can be found in Camelid mammals which are naturally devoid of light chains. Such VHH are also called "nanobody®". According to the invention, sdAb can particularly be llama sdAb. Sanofi-Genzyme has developed a blocking and depleting antibody SAR440241. R&D Systems has developed a blocking antibody MAB-160. This kind of antibodies affects mostly immune cells, notably the immune adaptive system and not melanocytes.

In a particular embodiment, the GD3 antibody includes but are not limited to the clone MB3.6 or the clone R24 or derivative from those clones (afucosylated, humanized . . . ). Examples of GD3 antibody includes but are not limited to Ganglioside GD3 Monoclonal Antibody of LifeSpan BioSciences, ST8 alpha-2,8-Sialyltransferase 8A/ST8SIA1/Ganglioside GD3 Antibody of Novus Biologicals, Ganglioside GD3 (2Q631) Antibody and Ganglioside GD3 (MB3.6) Antibody of Santa Cruz Biotechnology, Inc., Mab Moxhuman Ganglioside GD3 antibody of United States Biological, Mitumomab, Ecromeximab and clone U36 of Creative Biolabs.

In some embodiments, the GD3 inhibitor is a short hairpin RNA (shRNA), a small interfering RNA (siRNA) or an antisense oligonucleotide which inhibits the expression of GD3. In a particular embodiment, the antagonist of GD3 expression is siRNA. A short hairpin RNA (shRNA) is a sequence of RNA that makes a tight hairpin turn that can be used to silence gene expression via RNA interference. shRNA is generally expressed using a vector introduced into cells, wherein the vector utilizes the U6 promoter to ensure that the shRNA is always expressed. This vector is usually passed on to daughter cells, allowing the gene silencing to be inherited. The shRNA hairpin structure is cleaved by the cellular machinery into siRNA, which is then bound to the RNA-induced silencing complex (RISC). This complex binds to and cleaves mRNAs that match the siRNA to which it is bound. Small interfering RNA (siRNA), sometimes known as short interfering RNA or silencing RNA, are a class of 20-25 nucleotide-long double-stranded RNA molecules that play a variety of roles in biology. Most notably, siRNA is involved in the RNA interference (RNAi) pathway whereby the siRNA interferes with the expression of a specific gene. Anti-sense oligonucleotides include anti-sense RNA molecules and anti-sense DNA molecules, would act to directly block the translation of the targeted mRNA by binding thereto and thus preventing protein translation or increasing mRNA degradation, thus decreasing the level of the targeted protein, and thus activity, in a cell. For example, antisense oligonucleotides of at least about 15 bases and complementary to unique regions of the mRNA transcript sequence can be synthesized, e.g., by conventional phosphodiester techniques. Methods for using antisense techniques for specifically inhibiting gene expression of genes whose sequence is known are well known in the art (e.g. see U.S. Pat. Nos. 6,566,135; 6,566,131; 6,365,354; 6,410,323; 6,107,091; 6,046,321; and 5,981,732). Antisense oligonucleotides, siRNAs, shRNAs of the invention may be delivered in vivo alone or in association with a vector. In its broadest sense, a "vector" is any vehicle capable of facilitating the transfer of the antisense oligonucleotide, siRNA, shRNA or ribozyme nucleic acid to the cells and typically mast cells. Typically, the vector transports the nucleic acid to cells with reduced degradation relative to the extent of degradation that would result in the absence of the vector. In general, the vectors useful in the invention include, but are not limited to, plasmids, phagemids, viruses, other vehicles derived from viral or bacterial sources that have been manipulated by the insertion or incorporation of the antisense oligonucleotide, siRNA, shRNA or ribozyme nucleic acid sequences. Viral vectors are a preferred type of vector and include, but are not limited to nucleic acid sequences from the following viruses: retrovirus, such as Moloney murine leukemia virus, harvey murine sarcoma virus, murine mammary tumor virus, and rous sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors not named but known to the art.

In some embodiments, the GD3 inhibitor is an endonuclease. In the last few years, staggering advances in sequencing technologies have provided an unprecedentedly detailed overview of the multiple genetic aberrations in cancer. By considerably expanding the list of new potential oncogenes and tumor suppressor genes, these new data strongly emphasize the need of fast and reliable strategies to characterize the normal and pathological function of these genes and assess their role, in particular as driving factors during oncogenesis. As an alternative to more conventional approaches, such as cDNA overexpression or downregulation by RNA interference, the new technologies provide the means to recreate the actual mutations observed in cancer through direct manipulation of the genome. Indeed, natural and engineered nuclease enzymes have attracted considerable attention in the recent years. The mechanism behind endonuclease-based genome inactivating generally requires a first step of DNA single or double strand break, which can then trigger two distinct cellular mechanisms for DNA repair, which can be exploited for DNA inactivating: the error-prone nonhomologous end-joining (NHEJ) and the high-fidelity homology-directed repair (HDR).

In a particular embodiment, the endonuclease is CRISPR-cas. As used herein, the term "CRISPR-cas" has its general meaning in the art and refers to clustered regularly interspaced short palindromic repeats associated which are the segments of prokaryotic DNA containing short repetitions of base sequences.

In some embodiment, the endonuclease is CRISPR-cas9 which is from *Streptococcus* pyogenes. The CRISPR/Cas9 system has been described in U.S. Pat. No. 8,697,359 B1 and US 2014/0068797. Originally an adaptive immune system in prokaryotes (Barrangou and Marraffini, 2014), CRISPR has been recently engineered into a new powerful tool for genome editing. It has already been successfully used to target important genes in many cell lines and organisms, including human (Mali et al., 2013, Science, Vol. 339 : 823-826), bacteria (Fabre et al., 2014, PLoS Negl. Trop. Dis., Vol. 8:e2671.), zebrafish (Hwang et al., 2013, PLoS One, Vol. 8:e68708.), *C. elegans* (Hai et al., 2014 Cell Res. doi: 10.1038/cr.2014.11.), bacteria (Fabre et al., 2014, PLoS Negl. Trop. Dis., Vol. 8:e2671.), plants (Mali et al., 2013, Science, Vol. 339:823-826), *Xenopus tropicalis* (Guo et al., 2014, Development, Vol. 141 : 707-714.), yeast (DiCarlo et al., 2013, Nucleic Acids Res., Vol. 41 : 4336-4343.), Drosophila (Gratz et al., 2014 Genetics, doi:10.1534/genetics.113.160713), monkeys (Niu et al., 2014, Cell, Vol. 156 : 836-843.), rabbits (Yang et al., 2014, J. Mol. Cell Biol., Vol. 6 : 97-99.), pigs (Hai et al., 2014, Cell Res. doi: 10.1038/cr.2014.11.), rats (Ma et al., 2014, Cell Res., Vol. 24 : 122-125.) and mice (Mashiko et al., 2014, Dev. Growth Differ. Vol. 56 : 122-129.). Several groups have now taken advantage of this method to introduce single point mutations (deletions or insertions) in a particular target gene, via a single gRNA. Using a pair of gRNA-directed Cas9 nucleases instead, it is also possible to induce large deletions or genomic rearrangements, such as inversions or translocations. A recent exciting development is the use of the dCas9 version of the CRISPR/Cas9 system to target protein domains for transcriptional regulation, epigenetic modification, and microscopic visualization of specific genome loci.

In some embodiment, the endonuclease is CRISPR-Cpf1 which is the more recently characterized CRISPR from Provotella and Francisella 1 (Cpf1) in Zetsche et al. ("Cpf1 is a Single RNA-guided Endonuclease of a Class 2 CRISPR-Cas System (2015); Cell; 163, 1-13).

In some embodiments, the GD3 inhibitor is an aptamer. In a particular embodiment, aptamers are DNA aptamers such as described in Prodeus et al 2015. A major disadvantage of aptamers as therapeutic entities is their poor pharmacokinetic profiles, as these short DNA strands are rapidly removed from circulation due to renal filtration. Thus, aptamers according to the invention are conjugated to with high molecular weight polymers such as polyethylene glycol (PEG). In a particular embodiment, the aptamer is an anti-PD-1 aptamer. Particularly, the anti-PD-1 aptamer is MP7 pegylated as described in Prodeus et al 2015.

As used herein, the term "treatment" or "treat" refer to both prophylactic or preventive treatment as well as curative, improving the patient's condition or disease modifying treatment, including treatment of patient at risk of contracting the disease or suspected to have contracted the disease as well as patients who are ill or have been diagnosed as suffering from a disease or medical condition, and includes suppression of clinical relapse. The treatment may be administered to a subject having a medical disorder or who ultimately may acquire the disorder, in order to prevent, cure, delay the onset of, reduce the severity of, or ameliorate one or more symptoms of a disorder or recurring disorder, or in order to prolong the survival of a subject beyond that expected in the absence of such treatment. By "therapeutic regimen" is meant the pattern of treatment of an illness, e.g., the pattern of dosing used during therapy. A therapeutic regimen may include an induction regimen and a maintenance regimen. The phrase "induction regimen" or "induction period" refers to a therapeutic regimen (or the portion of a therapeutic regimen) that is used for the initial treatment of a disease. The general goal of an induction regimen is to provide a high level of drug to a patient during the initial period of a treatment regimen. An induction regimen may employ (in part or in whole) a "loading regimen", which may include administering a greater dose of the drug than a physician would employ during a maintenance regimen, administering a drug more frequently than a physician would administer the drug during a maintenance regimen, or both. The phrase "maintenance regimen" or "maintenance period" refers to a therapeutic regimen (or the portion of a therapeutic regimen) that is used for the maintenance of a patient during treatment of an illness, e.g., to keep the patient in remission for long periods of time (months or years). A maintenance regimen may employ continuous therapy (e.g., administering a drug at regular intervals, e.g., daily, weekly, monthly, yearly, etc.) or intermittent therapy (e.g., interrupted treatment, intermittent treatment, treatment at relapse, or treatment upon achievement of a particular predetermined criteria [e.g., disease manifestation, etc.]).

As used herein, the term "preventing" intends characterizing a prophylactic method or process that is aimed at delaying or preventing the onset of a disorder or condition to which such term applies.

As used herein the terms "administering" or "administration" refer to the act of injecting or otherwise physically delivering a substance as it exists outside the body (e.g. GD3 inhibitor) into the subject, such as by mucosal, intradermal, intravenous, subcutaneous, intramuscular delivery and/or any other method of physical delivery described herein or known in the art. When a disease, or a symptom thereof, is being treated, administration of the substance typically occurs after the onset of the disease or symptoms thereof. When a disease or symptoms thereof, are being prevented, administration of the substance typically occurs before the onset of the disease or symptoms thereof.

A "therapeutically effective amount" refers to an amount effective, at dosages and for periods of time necessary, to achieve a desired therapeutic result. A therapeutically effective amount of drug may vary according to factors such as the disease state, age, sex, and weight of the individual, and the ability of drug to elicit a desired response in the individual. A therapeutically effective amount is also one in which any toxic or detrimental effects of the antibody or antibody portion are outweighed by the therapeutically beneficial effects. The efficient dosages and dosage regimens for drug depend on the disease or condition to be treated and may be determined by the persons skilled in the art. A physician having ordinary skill in the art may readily determine and prescribe the effective amount of the pharmaceutical composition required. For example, the physician could start doses of drug employed in the pharmaceutical composition at levels lower than that required in order to achieve the desired therapeutic effect and gradually increase the dosage until the desired effect is achieved. In general, a suitable dose of a composition of the present invention will be that amount of the compound which is the lowest dose effective to produce a therapeutic effect according to a particular dosage regimen. Such an effective dose will generally depend upon the factors described above. For example, a therapeutically effective amount for therapeutic use may be measured by its ability to stabilize the progression of disease. One of ordinary skill in the art would be able to determine such amounts based on such factors as the subject's size, the severity of the subject's symptoms, and the particular composition or route of administration selected. An exemplary, non-limiting range for a therapeutically effective amount of drug is about 0.1-100 mg/kg, such as about 0.1-50 mg/kg, for example about 0.1-20 mg/kg, such as about 0.1-10 mg/kg, for instance about 0.5, about such as 0.3, about 1, about 3 mg/kg, about 5 mg/kg or about 8 mg/kg. Administration may e.g. be intravenous, intramuscular, intraperitoneal, or subcutaneous, and for instance administered proximal to the site of the target. Dosage regimens in the above methods of treatment and uses are adjusted to provide the optimum desired response (e.g., a therapeutic response). For example, a single bolus may be administered, several divided doses may be administered over time or the dose may be proportionally reduced or increased as indicated by the exigencies of the therapeutic situation. In some embodiments, the efficacy of the treatment is monitored during the therapy, e.g. at predefined points in time. As non-limiting examples, treatment according to the present invention may be provided as a daily dosage of the agent of the present invention in an amount of about 0.1-100 mg/kg, such as 0.2, 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of days 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least one of weeks 1, 2, 3, 4, 5, 6, 7, 8, 9, 10, 11, 12, 13, 14, 15, 16, 17, 18, 19 or 20 after initiation of treatment, or any combination thereof, using single or divided doses every 24, 12, 8, 6, 4, or 2 hours, or any combination thereof.

As used herein, the term "combination" is intended to refer to all forms of administration that provide a first drug together with a further (second, third . . . ) drug. The drugs may be administered simultaneously, separately or sequentially and in any order. According to the invention, the drug is administered to the subject using any suitable method that enables the drug to reach the chondrocytes of the bone growth plate. In some embodiments, the drug administered to the subject systemically (i.e. via systemic administration). Thus, in some embodiments, the drug is administered to the subject such that it enters the circulatory system and is distributed throughout the body. In some embodiments, the drug is administered to the subject by local administration, for example by local administration to the growing bone.

As used herein, the terms "combined treatment", "combined therapy" or "therapy combination" refer to a treatment that uses more than one medication. The combined therapy may be dual therapy or bi-therapy.

As used herein, the term "administration simultaneously" refers to administration of 2 active ingredients by the same route and at the same time or at substantially the same time. The term "administration separately" refers to an administration of 2 active ingredients at the same time or at substantially the same time by different routes. The term "administration sequentially" refers to an administration of 2 active ingredients at different times, the administration route being identical or different.

In some embodiments, the treatment consists of administering to the subject an immunotherapeutic agent. The term "immunotherapeutic agent", as used herein, refers to a compound, composition or treatment that indirectly or directly enhances, stimulates or increases the body's immune response against cancer cells and/or that decreases the side effects of other anticancer therapies. Immunotherapy is thus a therapy that directly or indirectly stimulates or enhances the immune system's responses to cancer cells and/or lessens the side effects that may have been caused by other anti-cancer agents. Immunotherapy is also referred to in the art as immunologic therapy, biological therapy biological response modifier therapy and biotherapy. Examples of common immunotherapeutic agents known in the art include, but are not limited to, cytokines, cancer vaccines, monoclonal antibodies and non-cytokine adjuvants. Alternatively the immunotherapeutic treatment may consist of administering the subject with an amount of immune cells (T cells, NK, cells, dendritic cells, B cells . . . ).

Immunotherapeutic agents can be non-specific, i.e. boost the immune system generally so that the human body becomes more effective in fighting the growth and/or spread of cancer cells, or they can be specific, i.e. targeted to the cancer cells themselves immunotherapy regimens may combine the use of non-specific and specific immunotherapeutic agents.

Non-specific immunotherapeutic agents are substances that stimulate or indirectly improve the immune system. Non-specific immunotherapeutic agents have been used alone as a main therapy for the treatment of cancer, as well as in addition to a main therapy, in which case the non-specific immunotherapeutic agent functions as an adjuvant to enhance the effectiveness of other therapies (e.g. cancer vaccines). Non-specific immunotherapeutic agents can also function in this latter context to reduce the side effects of other therapies, for example, bone marrow suppression induced by certain chemotherapeutic agents. Non-specific immunotherapeutic agents can act on key immune system cells and cause secondary responses, such as increased production of cytokines and immunoglobulins. Alternatively, the agents can themselves comprise cytokines. Non-specific immunotherapeutic agents are generally classified as cytokines or non-cytokine adjuvants.

A number of cytokines have found application in the treatment of cancer either as general non-specific immunotherapies designed to boost the immune system, or as adjuvants provided with other therapies. Suitable cytokines include, but are not limited to, interferons, interleukins and colony-stimulating factors.

Interferons (IFNs) contemplated by the present invention include the common types of IFNs, IFN-alpha (IFN-$\alpha$), IFN-beta (IFN-$\beta$) and IFN-gamma (IFN-$\gamma$). IFNs can act directly on cancer cells, for example, by slowing their growth, promoting their development into cells with more normal behaviour and/or increasing their production of antigens thus making the cancer cells easier for the immune system to recognise and destroy. IFNs can also act indirectly on cancer cells, for example, by slowing down angiogenesis, boosting the immune system and/or stimulating natural killer (NK) cells, T cells and macrophages. Recombinant IFN-alpha is available commercially as Roferon (Roche Pharmaceuticals) and Intron A (Schering Corporation).

Interleukins contemplated by the present invention include IL-2, IL-4, IL-11 and IL-12. Examples of commercially available recombinant interleukins include Proleukin® (IL-2; Chiron Corporation) and Neumega® (IL-12; Wyeth Pharmaceuticals). Zymogenetics, Inc. (Seattle, Wash.) is currently testing a recombinant form of IL-21, which is also contemplated for use in the combinations of the present invention.

Colony-stimulating factors (CSFs) contemplated by the present invention include granulocyte colony stimulating factor (G-CSF or filgrastim), granulocyte-macrophage colony stimulating factor (GM-CSF or sargramostim) and erythropoietin (epoetin alfa, darbepoietin). Treatment with one or more growth factors can help to stimulate the generation of new blood cells in subjects undergoing traditional chemotherapy. Accordingly, treatment with CSFs can be helpful in decreasing the side effects associated with chemotherapy and can allow for higher doses of chemotherapeutic agents to be used. Various-recombinant colony stimulating factors are available commercially, for example, Neupogen® (G-CSF; Amgen), Neulasta (pelfilgrastim; Amgen), Leukine (GM-CSF; Berlex), Procrit (erythropoietin; Ortho Biotech), Epogen (erythropoietin; Amgen), Arnesp (erytropoietin).

In addition to having specific or non-specific targets, immunotherapeutic agents can be active, i.e. stimulate the body's own immune response, or they can be passive, i.e. comprise immune system components that were generated external to the body.

Passive specific immunotherapy typically involves the use of one or more monoclonal antibodies that are specific for a particular antigen found on the surface of a cancer cell or that are specific for a particular cell growth factor. Monoclonal antibodies may be used in the treatment of cancer in a number of ways, for example, to enhance a subject's immune response to a specific type of cancer, to interfere with the growth of cancer cells by targeting specific cell growth factors, such as those involved in angiogenesis, or by enhancing the delivery of other anticancer agents to cancer cells when linked or conjugated to agents such as chemotherapeutic agents, radioactive particles or toxins.

In some embodiments, the subject will be treated with a GD3 inhibitor in combination with an immune checkpoint inhibitor.

In some embodiments, the therapy consists of administering to the subject an immune checkpoint inhibitor in combination with GD3 inhibitor.

In a particular embodiment, i) an immune checkpoint inhibitor and ii) GD3 inhibitor as a combined preparation according to the invention for simultaneous, separate or sequential use in the method for treating senescent cells accumulation related disease in a subject.

In some embodiments, the present invention relates to the induction of senescence in cancer cells with drugs followed by the treatment with Immune Checkpoint Inhibitors (ICI).

In some embodiments, the therapy consists of induction of senescence followed by administration to the subject an immune checkpoint inhibitor in combination with GD3 inhibitor.

As used herein, the term "immune checkpoint inhibitor" (ICI) refers to molecules that totally or partially reduce, inhibit, interfere with or modulate one or more immune checkpoint proteins. As used herein, the term "immune checkpoint protein" has its general meaning in the art and refers to a molecule that is expressed by T cells in that either turn up a signal (stimulatory checkpoint molecules) or turn down a signal (inhibitory checkpoint molecules). Immune checkpoint molecules are recognized in the art to constitute immune checkpoint pathways similar to the CTLA-4 and PD-1 dependent pathways (see e.g. Pardoll, 2012. Nature Rev Cancer 12:252-264; Mellman et al. 2011. Nature 480: 480-489). Examples of stimulatory checkpoint include CD27 CD28 CD40, CD122, CD137, OX40, GITR, and ICOS. Examples of inhibitory checkpoint molecules include A2AR, B7-H3, B7-H4, BTLA, CTLA-4, CD277, IDO, KIR, PD-1, LAG-3, TIM-3 and VISTA. The Adenosine A2A receptor (A2AR) is regarded as an important checkpoint in cancer therapy because adenosine in the immune microenvironment, leading to the activation of the A2a receptor, is negative immune feedback loop and the tumor microenvironment has relatively high concentrations of adenosine. B7-H3, also called CD276, was originally understood to be a co-stimulatory molecule but is now regarded as co-inhibitory. B7-H4, also called VTCN1, is expressed by tumor cells and tumor-associated macrophages and plays a role in tumour escape. B and T Lymphocyte Attenuator (BTLA) and also called CD272, has HVEM (Herpesvirus Entry Mediator) as its ligand. Surface expression of BTLA is gradually downregulated during differentiation of human CD8+ T cells from the naive to effector cell phenotype, however tumor-specific human CD8+ T cells express high levels of BTLA. CTLA-4, Cytotoxic T-Lymphocyte-Associated protein 4 and also called CD152. Expression of CTLA-4 on Treg cells serves to control T cell proliferation. IDO, Indoleamine 2,3-dioxygenase, is a tryptophan catabolic enzyme. A related immune-inhibitory enzymes. Another important molecule is TDO, tryptophan 2,3-dioxygenase. IDO is known to suppress T and NK cells, generate and activate Tregs and myeloid-derived suppressor cells, and promote tumour angiogenesis. KIR, Killer-cell Immunoglobulin-like Receptor, is a receptor for MHC Class I molecules on Natural Killer cells. LAG3, Lymphocyte Activation Gene-3, works to suppress an immune response by action to Tregs as well as direct effects on CD8+ T cells. PD-1, Programmed Death 1 (PD-1) receptor, has two ligands, PD-L1 and PD-L2. This checkpoint is the target of Merck & Co.'s melanoma drug Keytruda, which gained FDA approval in September 2014. An advantage of targeting PD-1 is that it can restore immune function in the tumor microenvironment. TIM-3, short for T-cell Immunoglobulin domain and Mucin domain 3, expresses on activated human CD4+ T cells and regulates Th1 and Th17 cytokines. TIM-3 acts as a negative regulator of Th1/Tc1function by triggering cell death upon interaction with its ligand, galectin-9. VISTA, Short for V-domain Ig suppressor of T cell activation, VISTA is primarily expressed on hematopoietic cells so that consistent expression of VISTA on leukocytes within tumors may allow VISTA blockade to be effective across a broad range of solid tumors. Tumor cells often take advantage of these checkpoints to escape detection by the immune system. Thus, inhibiting a checkpoint protein on the immune system may enhance the anti-tumor T-cell response.

In some embodiments, an immune checkpoint inhibitor refers to any compound inhibiting the function of an immune checkpoint protein. Inhibition includes reduction of function and full blockade. In some embodiments, the immune checkpoint inhibitor could be an antibody, synthetic or native sequence peptides, small molecules or aptamers which bind to the immune checkpoint proteins and their ligands.

In a particular embodiment, the immune checkpoint inhibitor is an antibody.

Typically, antibodies are directed against A2AR, B7-H3, B7-H4, BTLA, CTLA-4, CD277, IDO, KIR, PD-1, LAG-3, TIM-3 or VISTA.

In a particular embodiment, the immune checkpoint inhibitor is an anti-PD-1 antibody such as described in WO2011082400, WO2006121168, WO2015035606, WO2004056875, WO2010036959, WO2009114335, WO2010089411, WO2008156712, WO2011110621, WO2014055648 and WO2014194302. Examples of anti-PD-1 antibodies which are commercialized: Nivolumab (Opdivo®, BMS), Pembrolizumab (also called Lambrolizumab, KEYTRUDA® or MK-3475, MERCK).

In some embodiments, the immune checkpoint inhibitor is an anti-PD-L1 antibody such as described in WO2013079174, WO2010077634, WO2004004771, WO2014195852, WO2010036959, WO2011066389, WO2007005874, WO2015048520, U.S. Pat. No. 8,617,546 and WO2014055897. Examples of anti-PD-L1 antibodies which are on clinical trial: Atezolizumab (MPDL3280A, Genentech/Roche), Durvalumab (AZD9291, AstraZeneca), Avelumab (also known as MSB0010718C, Merck) and BMS-936559 (BMS).

In some embodiments, the immune checkpoint inhibitor is an anti-PD-L2 antibody such as described in U.S. Pat. Nos. 7,709,214, 7,432,059 and 8,552,154.

In the context of the invention, the immune checkpoint inhibitor inhibits Tim-3 or its ligand.

In a particular embodiment, the immune checkpoint inhibitor is an anti-Tim-3 antibody such as described in WO03063792, WO2011155607, WO2015117002, WO2010117057 and WO2013006490.

In some embodiments, the immune checkpoint inhibitor is a small organic molecule.

The term "small organic molecule" as used herein, refers to a molecule of a size comparable to those organic molecules generally used in pharmaceuticals. The term excludes biological macro molecules (e. g. proteins, nucleic acids, etc.). Typically, small organic molecules range in size up to about 5000 Da, more preferably up to 2000 Da, and most preferably up to about 1000 Da.

Typically, the small organic molecules interfere with transduction pathway of A2AR, B7-H3, B7-H4, BTLA, CTLA-4, CD277, IDO, KIR, PD-1, LAG-3, TIM-3 or VISTA.

In a particular embodiment, small organic molecules interfere with transduction pathway of PD-1 and Tim-3. For example, they can interfere with molecules, receptors or enzymes involved in PD-1 and Tim-3 pathway.

In a particular embodiment, the small organic molecules interfere with Indoleamine-pyrrole 2,3-dioxygenase (IDO) inhibitor. IDO is involved in the tryptophan catabolism (Liu et al 2010, Vacchelli et al 2014, Zhai et al 2015). Examples of IDO inhibitors are described in WO 2014150677. Examples of IDO inhibitors include without limitation 1-methyl-tryptophan (IMT), β-(3-benzofuranyl)-alanine, β-(3-benzo(b)thienyl)-alanine), 6-nitro-tryptophan, 6-fluoro-tryptophan, 4-methyl-tryptophan, 5-methyl tryptophan, 6-methyl-tryptophan, 5-methoxy-tryptophan, 5-hydroxy-tryptophan, indole 3-carbinol, 3,3'-diindolylmethane, epigallocatechin gallate, 5-Br-4-Cl-indoxyl 1,3-diacetate, 9-vinylcarbazole, acemetacin, 5-bromo-tryptophan, 5-bromoindoxyl diacetate, 3-Amino-naphtoic acid, pyrrolidine dithiocarbamate, 4-phenylimidazole a brassinin derivative, a thiohydantoin derivative, a β-carboline derivative or a brassilexin derivative. In a particular embodiment, the IDO inhibitor is selected from 1-methyl-tryptophan, β-(3-benzofuranyl)-alanine, 6-nitro-L-tryptophan, 3-Amino-naphtoic acid and β-[3-benzo(b)thienyl]-alanine or a derivative or prodrug thereof.

In a particular embodiment, the inhibitor of IDO is Epacadostat, (INCB24360, INCB024360) has the following chemical formula in the art and refers to —N-(3-bromo-4-fluorophenyl)-N'-hydroxy-4-{[2-(sulfamoylamino)-éthyl] amino}-1,2,5-oxadiazole-3 carboximidamide:

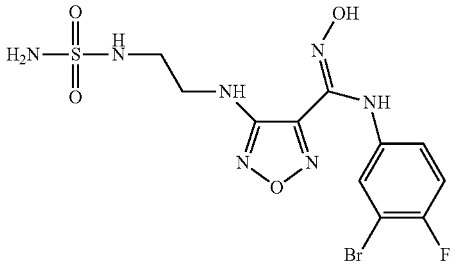 [SMILES: NS(=O)(=O)NCCNc1nonc1/C(=N/O)Nc1ccc(F)c(Br)c1]

In a particular embodiment, the inhibitor is BGB324, also called R428, such as described in WO2009054864, refers to 1H-1,2,4-Triazole-3,5-diamine, 1-(6,7-dihydro-5H-benzo[6,7]cyclohepta[1,2-c]pyridazin-3-yl)-N3-[(7S)-6,7,8,9-tetrahydro-7-(1-pyrrolidinyl)-5H-benzocyclohepten-2-yl]- and has the following formula in the art:

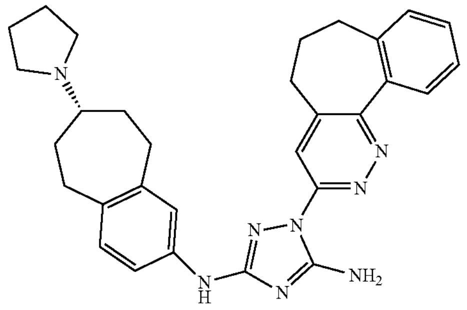 [SMILES: Nc1nc(Nc2ccc3c(c2)CC[C@@H](N2CCCC2)CC3)nn1-c1cc2c(nn1)-c1ccccc1CCC2]

In a particular embodiment, the inhibitor is CA-170 (or AUPM-170): an oral, small molecule immune checkpoint antagonist targeting programmed death ligand-1 (PD-L1) and V-domain Ig suppressor of T cell activation (VISTA) (Liu et al 2015). Preclinical data of CA-170 are presented by Curis Collaborator and Aurigene on November at ACR-NCI-EORTC International Conference on Molecular Targets and Cancer Therapeutics.

In some embodiments, the immune checkpoint inhibitor is an aptamer.

Typically, the aptamers are directed against A2AR, B7-H3, B7-H4, BTLA, CTLA-4, CD277, IDO, KIR, PD-1, LAG-3, TIM-3 or VISTA.

In a particular embodiment, aptamers are DNA aptamers such as described in Prodeus et al 2015. A major disadvantage of aptamers as therapeutic entities is their poor pharmacokinetic profiles, as these short DNA strands are rapidly removed from circulation due to renal filtration. Thus, aptamers according to the invention are conjugated to with high molecular weight polymers such as polyethylene glycol (PEG). In a particular embodiment, the aptamer is an anti-PD-1 aptamer. Particularly, the anti-PD-1 aptamer is MP7 pegylated as described in Prodeus et al 2015.

Typically, the GD3 inhibitor as described above are administered to the subject in the form of a pharmaceutical composition which comprises a pharmaceutically acceptable carrier. Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. For use in administration to a subject, the composition will be formulated for administration to the subject. The compositions of the present invention may be administered orally, parenterally, by inhalation spray, topically, rectally, nasally, buccally, vaginally or via an implanted reservoir. The used herein includes subcutaneous, intravenous, intramuscular, intra-articular, intra-synovial, intrasternal, intrathecal, intrahepatic, intralesional and intracranial injection or infusion techniques. Sterile injectable forms of the compositions of this invention may be aqueous or an oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono-or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation. The compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include, e.g., lactose. When aqueous suspensions are required for oral use, the active ingredient is combined with emulsifying and suspending agents. If desired, certain sweetening, flavoring or coloring agents may also be added. Alternatively, the compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols. The compositions of this invention may also be administered topically, especially when the target of treatment includes areas or organs readily accessible by topical application, including diseases of the eye, the skin, or the lower intestinal tract. Suitable topical formulations are readily prepared for each of these areas or organs. For topical applications, the compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water. Topical application for the lower intestinal tract can be effected in a rectal suppository formulation (see above) or in a suitable enema formulation. Patches may also be used. The compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents. For example, an antibody present in a pharmaceutical composition of this invention can be supplied at a concentration of 10 mg/mL in either 100 mg (10 mL) or 500 mg (50 mL) single-use vials. The product is formulated for IV administration in 9.0 mg/mL sodium chloride, 7.35 mg/mL sodium citrate dihydrate, 0.7 mg/mL polysorbate 80, and Sterile Water for Injection. The pH is adjusted to 6.5. An exemplary suitable dosage range for an antibody in a pharmaceutical composition of this invention may between about 1 $mg/m^2$ and 500 $mg/m^2$. However, it will be appreciated that these schedules are exemplary and that an optimal schedule and regimen can be adapted taking into account the affinity and tolerability of the particular antibody in the pharmaceutical composition that must be determined in clinical trials. A pharmaceutical composition of the invention for injection (e.g., intramuscular, i.v.) could be prepared to contain sterile buffered water (e.g. 1 ml for intramuscular), and between about 1 ng to about 100 mg, e.g. about 50 ng to about 30 mg or more preferably, about 5 mg to about 25 mg, of the inhibitor of the invention.

The invention will be further illustrated by the following figures and examples. However, these examples and figures should not be interpreted in any way as limiting the scope of the present invention.

FIGURES

FIG. 1: The natural GD3 expression by senescent cells directly determine their NK cell mediated immune surveillance. in vitro co-culture experiment using either replicative senescent cells knock-down for ST8SIA1 (A) or replicative senescent cells in presence of anti-GD3 monoclonal antibody or isotypic control (B). Data represent the mean of n=4 independent experiments, $*p<0.05$, $p<0.01$, and $*p<0.001$ ; Mann-Whitney test.

Figure 2:
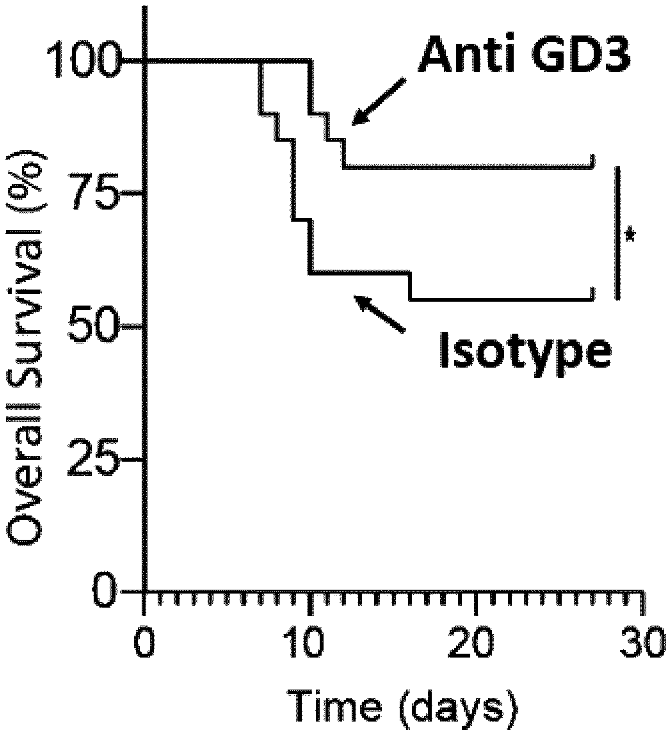

FIG. 2: GD3 targeting in vivo increases overall survival and reduces lung fibrosis lesions by restoring NK cell mediated immune surveillance locally. Overall survival analysis of fibrotic mice depending on mAb treatment. All experiments are performed with n=8 mice per group; *p<0.05, p<0.01, and *p<0.001; Mann-Whitney test.

Figure 3A:
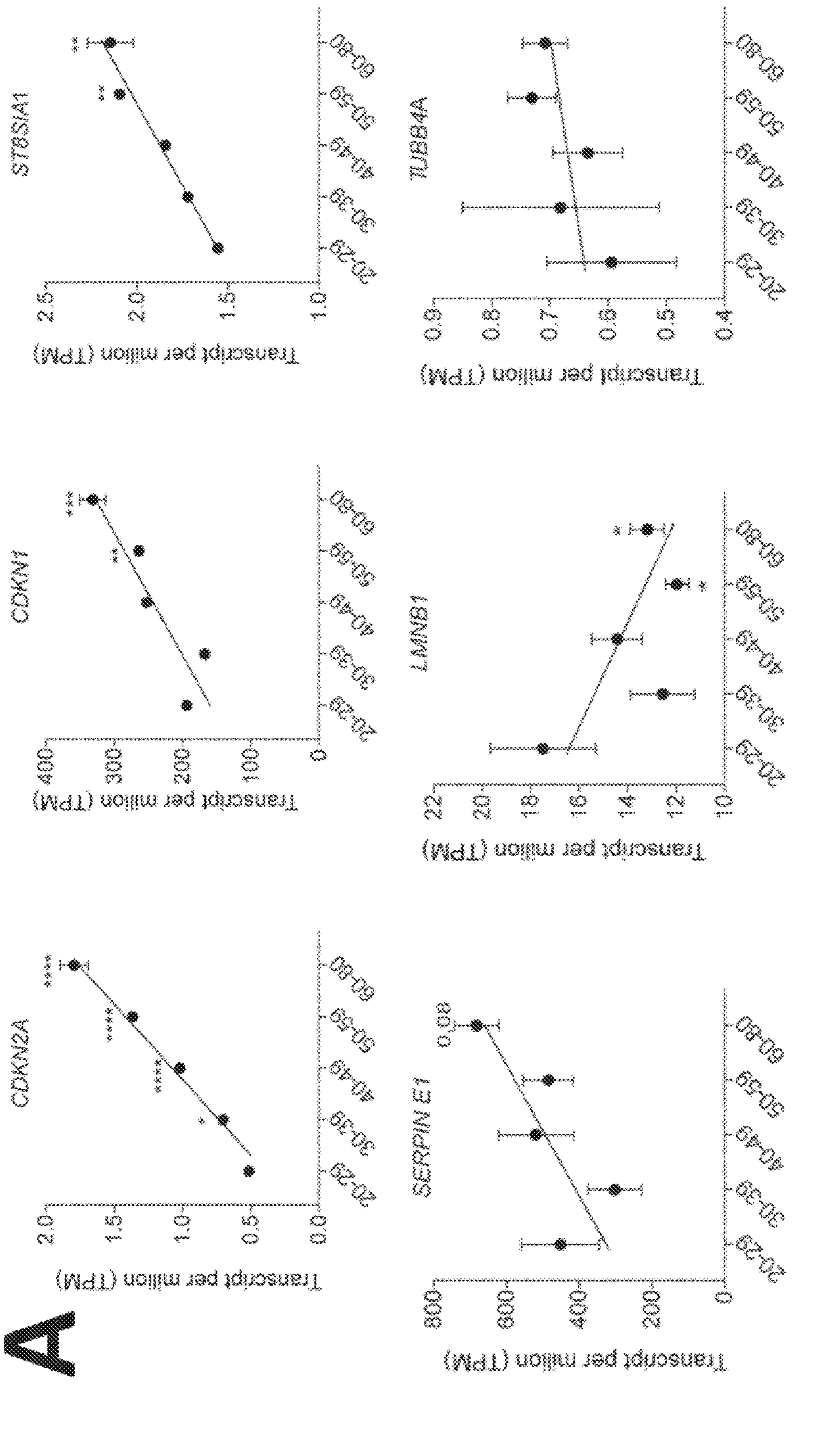
Figure 3B:
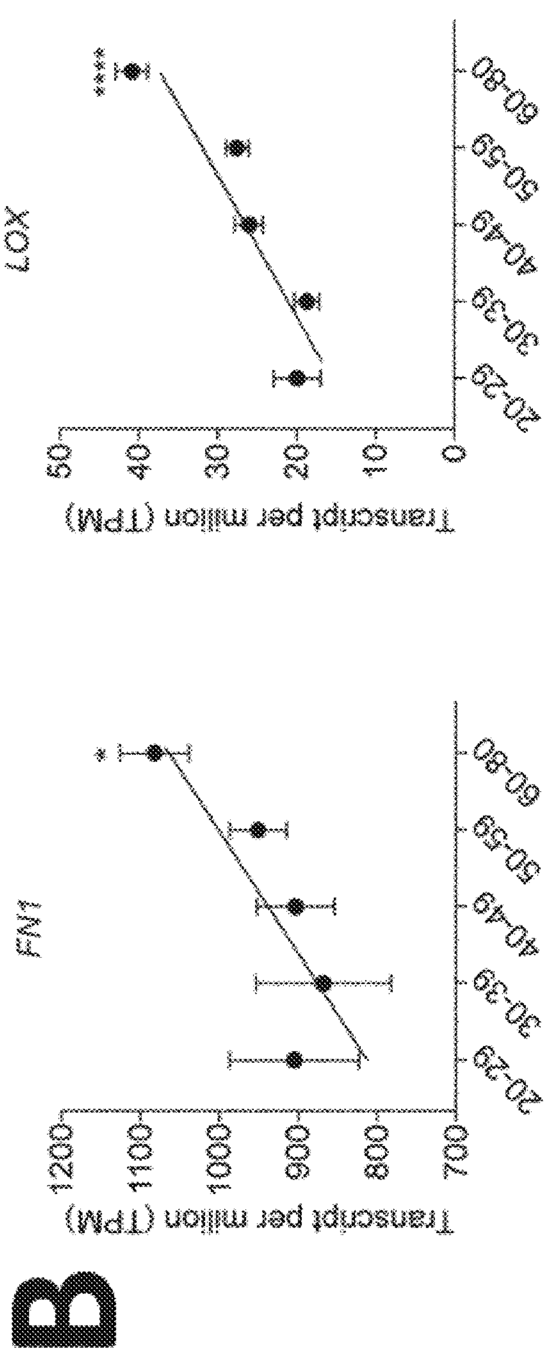
Figures 3C, 3D, 3E, 3F:
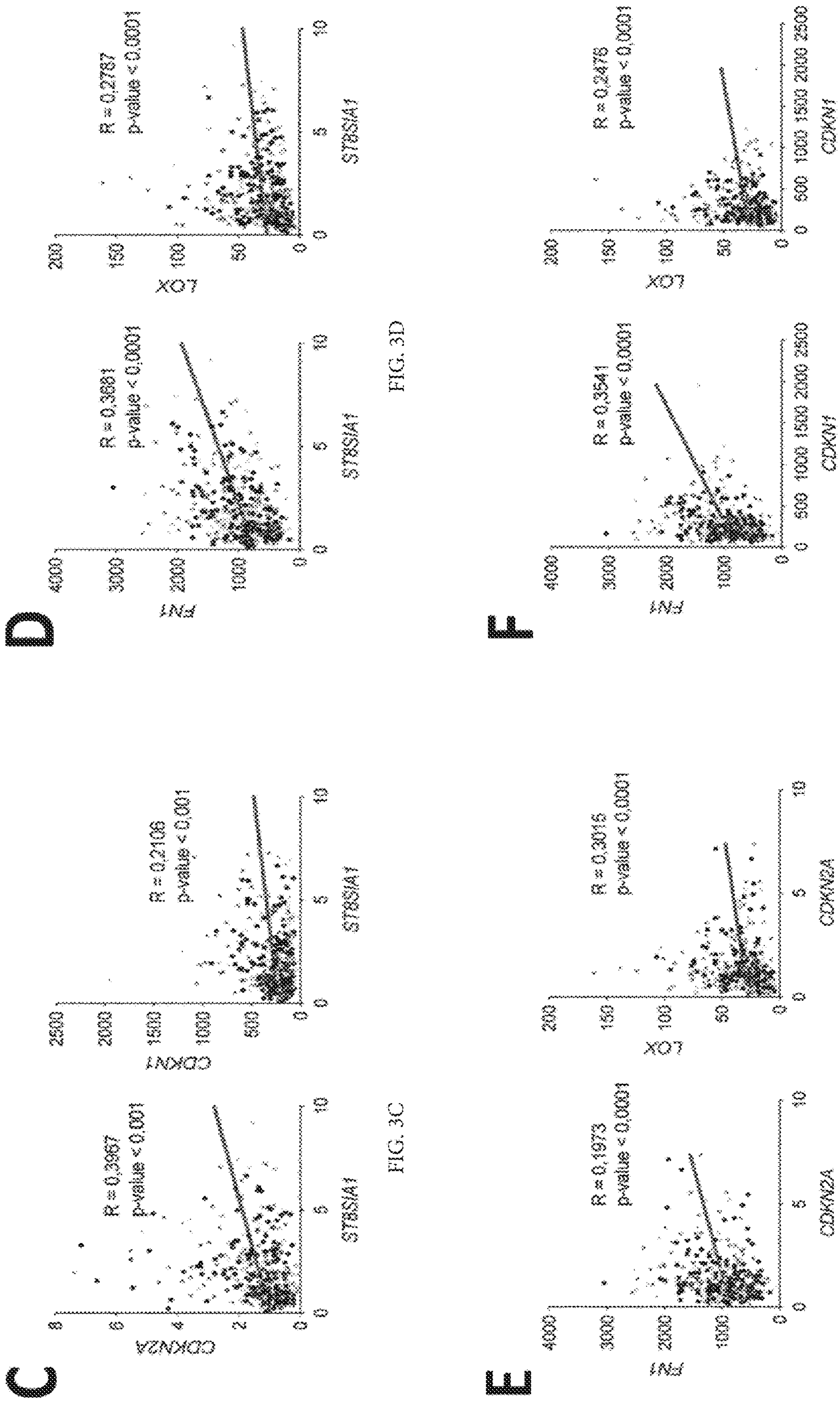

FIG. 3: ST8SIA1 expression is increased during human lung aging and correlates with the expression of senescence markers upon aging. (A), (B) Analysis of gene expression by RNAseq of normal human lung samples from different ages. Data are extracted from GTEX consortium and the relative gene expression (transcript per million or TPM) is represented in function of the group of age for senescence associated genes (A) or fibrosis associated genes (B). *p<0.05, p<0.01, and *p<0.001; two-way Anova test. c-f, Gene expression correlation (in TPM) between ST8SIA1 and CDKN2A or CDKN1 gene expression (C); ST8SIA1 and FN1 or LOX (D); CDKN2A and FN1 or LOX (E); or CDKN1 and FN1 or LOX (F). Data represent the Pearson uncentred correlation.

FIG. 4: Low-grade lung fibrosis appearing with aging is correlated with increased expression of GD3. (A), (B) Quantification of collagen deposition (A) and GD3 expression in lungs (B). All experiments are performed with n=8 mice per group. *p<0.05, p<0.01, and *p<0.001; Mann-Whitney U test.

Figure 5:
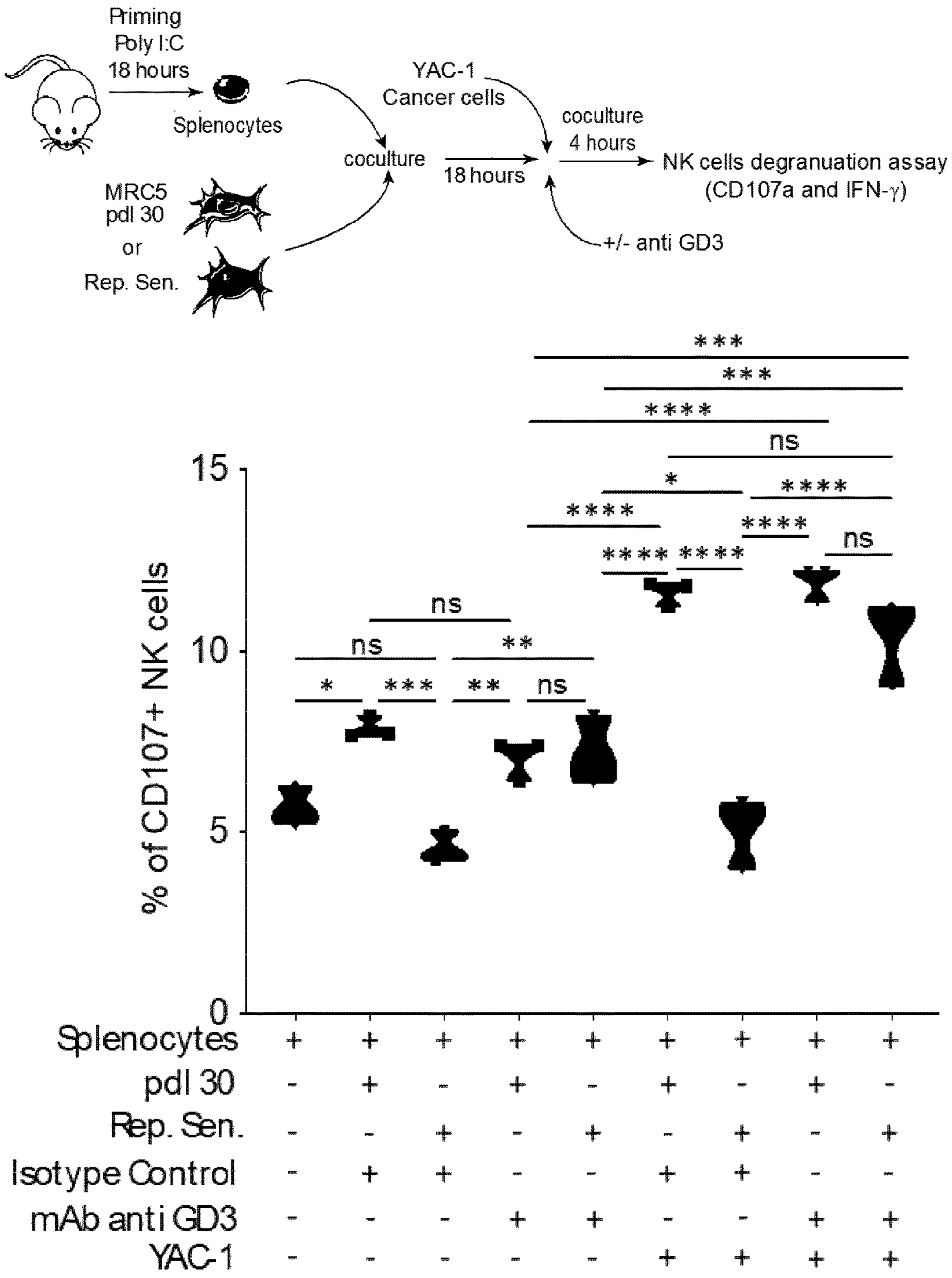

FIG. 5: Pre-exposure of NK cells to senescent GD3+ cells completely inhibit their anti-tumor capacity in a secondary challenge. NK cells were cultured with SnCs expressing GD3 or young cells that do not naturally expres GD3. These SnCs or young cells were derived from the same cell type (MRC5) and from the same cell production. After 18 hours of cocultures, cancer cells immunoactivating for NK cells (YAK1) were added to this first coculture for 18 hours in the presence or not of an anti-GD3 antibody. Finally, the functionality of NK cells was measured by determining their ability to degranulate (% of CD107a+ NK cells). The presence of senescent GD3+ cells totally inhibited the anti-tumor capacities of the NK cells and the addition of the anti GD3 antibody totally rescued them. *p<0.05, p<0.01, and *p<10 0.001; Man-Whitney test.

EXAMPLE

Material & Methods

Induction of Senescence

Replicative senescence was induced by continuous passaging of primary human fibroblasts MRC5 at 5% O2 until they reached a plateau in their growth curve. Cumulative population doublings level (PDL) was calculated using the following equation:

$$PDL = \frac{\log n_c - \log n_s}{\log 2}$$

where nc represents the number of cells counted after expansion and ns represents the number of cells seeded. Primary human fibroblasts MRC5 were induced to senesce by exposure to X-ray radiation at a total dose of 10 Gy at a rate of 5 Gy/min, treated with Nutlin 3a at 10 μM for 24 h, CCN1 2.5 μg/mL for 6 days, Bleomycin during 24 h at 50 μg/mL and Aphidicolin during 24 h at 2.5 μg/mL. Oncogene-Induced senescence was induced in hMEC human mammary epithelial cells transduced with a vector expressing H-RASG12V. Cells were treated with doxycycline hyclate (Sigma-Aldrich) at 1 μg/mL to activate H-RASG12V during 5 or 12 days.

Mycoplasma test was performed every month, and experiments are performed only on mycoplasma negative cells.

Animals. Matrigel Plug assays. Experiments are performed on 8- to 10-week-old female NMRI Nude mice from Charles River. 500 000 cells in 100 μl of PBS or the equivalent of the supernatant of the same cells concentrated by Amicon 10KD (Milipore) in 100 μl of PBS and complemented with 400 ul of Matrigel growth factor reduced (Corning) were inoculated subcutaneously into the back under isoflurane anesthesia. Five days after, mice were sacrificed and Matrigel plugs were harvested. Infiltrating cells were collected after enzymatic dissociation by Dispase (Corning), collagenase A, and DNAse I (Roche) digestion for 30 min at 37° C. Infiltrating cells stained with directly coupled antibodies for 30 min at 4° C. after saturation with Fc-Block anti-CD16/CD32 antibodies (clone 2.4G2) for 15 min on ice. After washes in 0.5 mM EDTA 2% FCS PBS, cells were analyzed using an ARIA III cytometer BD Biosciences with DIVA6 software and FlowJo 10 software. Mouse model of ADR-induced kidney injury. A single dose of 12 mg/kg of Adriamycin (ADR, Doxorubicin Hydrochloride, Sigma, Ref# D1515) was injected in tail vein of 3 months old BALB/c mice (Charles River). Littermates were injected similarly with saline (NaCl 0.9%). All mice were weighed twice a week in the time course of the experiments, and urine was collected for each individual mouse twice a week. Kidneys of the mice were collected 14 days after injection for further histological analysis. BALB/c mice were obtained from Janvier Lab (strain BALB/cJRj). Bleomycin induced lung fibrosis. 8- to 10-week-old pathogen-free female C57BL/6 mice (Charles River) were treated with intratracheal instillation of 50 μl of phosphate-buffered saline (PBS) or bleomycin (2.5 U.kg-1, Sigma-Amdrih). Animals were maintained in a 12:12-h light-dark cycle with food and water ad libitum. After the experiments, mouse lung tissues were excised and either included in OCT frozen, or inflated with 4% (w/v) paraformaldehyde in PBS, embedded in paraffin, sectioned, and stained with H&E and picrosirius red. The percent of tissue area that was classified as fibrosis was quantified with Image J. Alternatively, lungs were freshly dissociated with Miltenyi Lung dissociation Kit (ref 130-905-927) and GentleMacs with Heaters. Infiltrating cells stained with directly coupled antibodies for 30 min at 4° C. after saturation with Fc-Block anti-CD16/CD32 antibodies (clone 2.4G2) for 15 min on ice. After washes in 0.5 mM EDTA 2% FCS PBS, cells were analyzed using an ARIA III cytometer BD Biosciences with DIVA6 software and FlowJo 10 software. All mouse experiments were conducted according to local and international institutional guidelines and were approved by either the Animal Care Committee of the IRCAN and the regional (CIEPAL Côte d'Azur Agreements NCE/2015-266#2015102215087555 and NCE/2020-675# 2020042723583497) and national (French Ministry of Research) authorities.

Senescence-Associated β-Galactosidase Staining

Cells were fixed and stained using the Senescence-Associated β-Galactosidase Staining Kit (Abeam ab65351), following the manufacturer's instructions. After staining, cells were incubated for 12-14 h at 37° C., then visualised by phase-contrast microscopy.+calculation% beta gal+cells Senescence-Associated β-Galactosidase Staining on Cultured Cells.

Cells were fixed and stained using the Senescence-Associated β-Galactosidase Staining Kit (Abeam ab65351), following the manufacturer's instructions. After staining, cells were incubated for 12-14 h at 37° C., then visualized by phase-contrast microscopy. The percentage of Senescence-Associated β-Galactosidase-positives cells is calculated by determining the ratio of Senescence-Associated β-Galactosidase-positives cells (blue staining) among all cells counted. A minimum of 150 cells is counted for each condition at each experiment using the proliferative MRC5 (PDL30) as a negative control.

EdU Proliferation Assay on Cultured Cells.

To measure cell proliferation, an EdU (5-ethynyl-2-deoxyuridine) proliferation assay was performed as recommended by Thermo Fisher Scientific. MRC5 and hMEC cells were plated in 24-well plates at a density of 5×104 cells/well for 12 hours. Then incubated in serum-free DMEM containing 10 μmol/L EdU (Invitrogen/Click-IT EdU Alexa Fluor 647 Imaging Kit) for 12 hrs. Cells were fixed, then underwent DNA staining, according to the manufacturer's instructions to detect the number of cycling cells during the EdU treatment. The cells were imaged using confocal fluorescence microscopy (Zeiss LSM880) and the number of proliferating cells was averaged to calculate the percentage of proliferative cells. The percentage of proliferative cells is determined by calculating the ratio of the number of proliferating cells (EdU positive/red nucleus) to the total number of cells counted (DAPI+). A minimum of 100 cells is counted for each condition at each experiment using the proliferative MRC5 (PDL30) as a positive control.

Extraction and Purification of Glycolipids.

Cells (2×107) were lyophilized and extracted three times with CHCl3/CH3OH (2:1, v/v) and once by CHCl3/CH3OH (1:2, v/v) using intermediary centrifugations at 2500 g for 20 min. Combined supernatants were dried under a nitrogen stream, subjected to mild saponification in 0.1 M NaOH in CHCl3/CH3OH (1:1, v/v) at 37° C. for 2 h and evaporated to dryness. Samples were reconstituted in CH3OH/0.1% TFA in water (1:1, v/v) and applied to a reverse phase C18 cartridge (Waters, Milford, MA, USA) equilibrated in the same solvent. After washing with CH3OH/0.1% TFA in water (1:1, v/v), GSL were eluted by CH3OH, CHCl3/CH3OH (1:1, v/v) and CHCl3/CH3OH (2:1, v/v). The elution fraction was dried under nitrogen stream prior to structural analysis.

Sequential Release and Purification of N- and O-Glycans.

Cells were resuspended in 6 M guanidinium chloride and 5 mM EDTA in 0.1 M Tris/HCl, pH 8.4, and agitated for 4 h at 4° C. Then, dithiothreitol were added to a final concentration of 20 mM and incubated during 5 h at 37° C., followed by addition of 50 mM iodoacetamide overnight in the dark at room temperature. The reduced/alkyled glycoproteins were dialyzed against water at 4° C. for 72 h and lyophilized. Samples were incubated with trypsin TPCK (Sigma-Aldrich) at a 20:1 ratio (w/w) in 50 mM NH4HCO3, pH 8.5, for 24 h at 37° C. The digestion was stopped by incubation at 100° C. for 5 min, followed by C18 Sep-Pak chromatography (Waters Corp., Guyancourt, France). C18 Sep-Pak was equilibrated in 5% aqueous acetic acid and washed in the same solvent. Sample was loaded on the C18 Sep-Pak and the bound peptides were eluted with 20%, 40% and 60% (v/v) propanol in 5% aqueous acetic acid, pooled and lyophilized. N-Glycans were released by 10 U N-glycosidase F (Roche) digestion in 50 mM NH4HCO3 buffer pH 8.4, overnight at 37° C. N-glycans and O-glycopeptides were separated by C18 Sep-Pak, following the same protocol described above. Propanol fractions, containing O-glycopeptides, were pooled and freeze-dried. To liberate O-glycans, peptides were submitted to reductive elimination in 1 M NaBH4 and 0.1 M NaOH at 37° C. for 72 h. The reaction was stopped by the addition of Dowex 50×8 cation-exchange resin (25-50 mesh, H+ form) until pH 6.5 was reached. After evaporation to dryness, boric acid was distilled in the presence of methanol. Total material was then submitted to cation-exchange chromatography on a Dowex 50×2 column (200-400 mesh, H+ form) to remove residual peptides.

Mass Spectrometry.

Glycans and glycolipids were permethylated according to the method of Ciucanu and Kerek21 prior to mass spectrometry analysis. Briefly, samples were incubated with DMSO/NaOH/ICH3 during 2 h under sonication. The reaction was stopped with water and the permethylated glycans were extracted in CHCl3 and washed at least seven times with water. Permethylated glycans were solubilized in CHCl3 and mixed with 2,5-dihydroxybenzoic acid matrix solution (10 mg/mL dissolved in CHCl3/CH3OH (1:1, v/v) and spotted on MALDI plate. MALDI-TOF mass spectra were acquired on Voyager Elite DE-STR mass spectrometer (Perspective Biosystems, Framingham, MA, USA) and MALDITOF/TOF analyzed on 4800 Proteomics Analyzer mass spectrometer (Applied Biosystems, Framingham, MA, USA) in reflectron positive mode by delayed extraction using an acceleration mode of 20 kV, a pulse delay of 200 ns and grid voltage of 66%. For each spectrum, 5000 laser shots were performed and accumulated.

Immunofluorescence.

To analyze the presence of the ganglioside GD3 at the cell surface of MRC5, we seed 5.104 cells in the 24 wells plate. Cells were fixed during 10 minutes at room temperature with the 1×PBS solution containing 4% Formaldehyde (Sigma). For the GD3 staining, we use a primary antibody anti-GD3 R24 (Abcam) at 1:1000, overnight at 4° C. A secondary antibody against mouse whole IgG in FITC is used at 1:3000 during 1 hour at room temperature (Jackson ImmunoResearch). The autofluorescence of senescent cells was reduced by the utilization of Autofluorescence Eliminator Staining (Merck Millipore) staining following the manufacturer's instructions. The analysis was performed using fluorescence microscopy and used the same time of laser exposure between all the conditions.

Western Blotting.

Cells were harvested by trypsinization, washed in PBS and lysed with radio-immunoprecipitation assay (RIPA) buffer (Sigma-Aldrich) supplemented with protease and phosphatase inhibitors (Sigma-Aldrich) for 30 min on ice. Protein concentrations were determined using the BCA Protein Assay Kit (Interchim). Cell lysates (40 μg of the total protein) were diluted in SDS sample buffer with reducing agent (NuPage, Life Technologies) and boiled for 5 min at 95° C. Cell lysates were separated by protein electrophoresis at 150 V for 1 h using 4-20% Mini-Protean TGX pre-cast gels (BioRad) and transferred by semi-dry technic onto Amersham Hybond-P PVDF membranes (GE Healthcare). After blocking, membranes were probed with primary antibodies overnight at 4° C., washed and incubated with HRP-conjugated secondary antibodies (Vector, 1:20000) for 1 h at room temperature. Antibodies were detected using the ECL detection kit (GE Healthcare). Prior to re-probing with different antibodies, membranes were stripped at 4° C. in agitation using Antibody stripping buffer 1× for 10 minutes (Gene Bio-Application). Protein bands were quantified using ImageJ software. The integrated density of each band was measured using the gel analysis function of ImageJ, normalized to alpha-tubulin. Primary antibodies were mouse monoclonal anti-ganglioside GD3 R24 (Abcam), mouse monoclonal alpha-tubulin (Sigma).

Quantitative Real-Time PCR

Total RNA isolation from cells was performed using Trizol (Sigma-Aldrich). Reverse transcription (RT) was performed with the High-Capacity RNA to DNA kit (Applied Biosystems). Quantitative real-time PCR was performed on a Step-One Plus real-time system (Applied Biosystems) according to the manufacturer's protocol. qPCRs were made on cDNAs obtained using Roche's Fast Start Universal SYBR Green. Data were analyzed according to the Pfaffl method after calculation of primer efficiency. RPL0 was used as an endogenous control. All reactions were performed in triplicate, and at least 3 independent experiments were performed to generate each data set. The primers were as follows:

```
hST8SIA1 sense
                                        (SEQ ID NO: 1)
5'- GGGTGAGGCAAGTTGAAAGG-3';

hST8SIA1 antisense
                                        (SEQ ID NO: 2)
3'- AGGTCCTCAGCGAATTTCCA-5';

RPL0 sense
                                        (SEQ ID NO: 3)
5' -AACTCTGCATTCTCGCTTCCT-3';

RPL0 antisense
                                        (SEQ ID NO: 4)
3'- ACTCGTTTGTACCCGTTGATG-5';
```

GD3 Dosage by ELISA.

Serum from young (3 months-old) or old (24 months -old) mice or supernatant from young MRC5 until replicative senescent MRC5 were collected. The amount of free GD3 in sera or supernatants were assessed by ELISA against GD3 following the recommendation of the manufacturer (CUSABIOTECH ref CSB-EQ027866HU).

Coculture Experiment

Splenocytes are extract from C57B1/6j naïve mice previously stimulated in vivo for 14 h by an intraperitoneal injection of 150 μg of Poly I:C (Invivogen). The MRC5 are plated at 5×104 cells/well in 48 wells plate the day before the experiment for the good adherence of the cells. All the coculture were performed with four different mice at each time. Then, the killing capacity of NK cells was tested when they coculture with senescent/young or modulated for ST8SIA1 expression MRC5.NK cells are added to the culture for 4 h in presence of monensin and brefeldin (BD Biosciences) at the effector/target ratio of 1:1. Degranulation activity of the NK cells is then measured by FACS by the anti-CD107a (FITC BD Biosciences) and IFN-staining (PE BD Biosciences)

Ex Vivo Rechallenge Experiment.

Primary cells from the spleen (crushing on cell strainer 70 μm) or from the lungs (dissociation with Miltenyi Lung dissociation Kit ref 130-905-927 and GentleMacs with Heaters) were extracted from PBS or Bleomycin instillated mice. Bulk of primary cells (either from the spleen or the lungs) were then rechallenge in vitro with YAK-1 cells for 4 hours in presence of monensin and brefeldin (BD Bioscience) at the Effector/Target ratio of 5:1. Degranulation activity of the NK cells is then measured by FACS by the anti-CD107a and IFN-γ staining.

Real-Time NK Cell Cytotoxic Assay.

A real-time cytotoxic assay was performed as previously described22,23. Briefly, target cells were labelled with 0.5 μM Calcein-AM (Molecular Probes) for 15 min at room temperature. Proliferative or repmicative senescent MRC5 cells were additionally treated with 100 μM Indomethacin (Sigma Aldrich) to block multidrug-resistance transporters that expulse calcein. The inhibitor was maintained in the medium during the assay. Human primary NK cells purified from PBMC from healthy donors after FACS sorting. Calcein-labelled targets were incubated with human NK cells for 4 h at 37° C., 5% CO2 and real-time monitoring of NK cell killing was performed on a Cytation™ 5 (Biotek). Cell images were processed using GEN5 software (Biotek). The percentage of lysis from triplicates was calculated as follow: % lysis={1−[(experimental well at t/experimental well at t0)/(control well at t/control well at t0)]}×100.

In-vivo lung imaging by computed tomography (μCT). High-resolution CT scan were performed using a dedicated system (eXplore speCZT CT120, GE Healthcare). Mice were gas anesthetized (air and 1-2% isoflurane) in an air-warmed imaging chamber (Minerve) to maintain body temperature during the scanning time. Micro-CT image acquisition consisted of 400 projections collected in one full rotation of the gantry in approximately 5 min in a single bed focused on the lungs, with a 450 mA/80kV X-ray tube. 2-D and 3-D images were obtained and analyzed using the software program MicroView (GE Healthcare).

Senescence-Associated β-Galactosidase Staining and DNA Damage Analysis at Telomeres (Telomere Induced Foci) by ImagestreamX Analysis.

Cells were resuspended (either cells in culture or primary cells after tissues digestion) in phosphate-buffered saline (PBS), then were fixed with 4% paraformaldehyde (PFA) for 15 min at room temperature and stained using the Senescence-Associated β-Galactosidase Staining Kit (Abcam ab65351), following the manufacturer's instructions. After staining, cells were incubated for 12-14 h at 37° C. sealed and protected from light. After washes, cells were analyzed by ImageStreamX or permeabilized with PBS-TritonX100 (0.5%) and incubated 10 minutes at RT, then at 87° C. for 10 minutes while vortexing, and overnight at room temperature protected from light with (70% formamide, 1% blocking reagent, 10 mM Tris ph 7.2, 4 nM PNA probe-FITC). Cells were stained with specific antibody for 53BP1 (1/300) (Novus Biological) then incubated with Goat anti Rabbit Alexa 647 (1/900) (Jackson ImmunoResearch). Nucleus were stained with Hoeuchst (1/2000) then cells were washed twice and analyzed by ImageStreamX.

Histology & Immunohistochemistry.

Antigen retrieval was performed on 5 μm paraffin sections using Vector unmasking reagent (Vector Laboratories, Ref# H3300). Tissue sections were blocked (MOM kit, Vector Laboratories, Ref #BMK-2202), and incubated with mouse monoclonal anti-GD3 antibody (Abcam ab11779, 1:40) for overnight at 4° C. Primary antibody was detected using a biotinylated anti-mouse IgG (MOM kit, Vector Laboratories, Ref #BMK-2202) followed by streptavidin-Cy3 (Jackson ImmunoResearch, Ref #016-160-084). For fibrosis analysis, slides were stained with picro-sirius red solution for 1 h and washed with acetic acid solution and absolute alcohol before imaging in white light or polarized light.

Image analysis using ImageJ software. Stained tissue sections were sequentially scanned using an HD Zeiss microscope allowing imaging of the entire section. For signal analysis, all glomeruli (about 120) were manually demarcated within each kidney section. Quantification of the signal within glomeruli or within the remaining area of the kidney was performed using Image J software.

| Antibodies | | | | | | |
|---|---|---|---|---|---|---|
| Specificity | Company | Clone | Species | Isotype | Fluorochrome | Reference |
| anti Ly6G (Gr1) | eBioscience | RB6-8C5 | rat | IgG2b, k | PE | 12-5931-82 |
| anti CD107a | BD Biosciences | 1D4B | Rat | IgG2a/k | FITC | 553793 |
| anti CD11b | BD Biosciences | M1/70 | Rat | IgG2b | APC-H7 | 550993 |
| Anti CD11c | BD Biosciences | HL3 | Hamster | IgG1 | FITC | 557400 |
| anti CD19 | BD Biosciences | 1D3 | rat | IgG2a, κ | FITC | 553785 |
| Anti NKp46 | BD Biosciences | 29A1.4 | Rat | IgG2a | PE | 560757 |
| Anti CD45 | BD Biosciences | 30-F11 | Rat | IgG2b | PerCP | 557235 |
| Anti CD45 | BD Biosciences | 30-F11 | Rat | IgG2b | A700 | 560510 |
| Anti CD69 | BD Biosciences | H1.2F3 | Hamster | IgG1/K | PE-Cy7 | 552879 |
| anti CD8a | BD Biosciences | 53-6.7 | rat | IgG2a,K | BV650 | 563152 |
| anti IFN-γ | BD Biosciences | 4S.B3 | Mouse | IgG1/K | PE | 554552 |
| anti IFN-γ | BD Biosciences | XMG1.2 | Rat | IgG1/K | PE | 554412 |
| anti NK-1.1 | BD Biosciences | PK136 | Mouse | IgG2a/k | APC | 550627 |
| anti NK-1.1 | Biolegend | PK136 | Mouse | IgG2a, κ | APC | 108710 |
| Anti NKp46 | BD Biosciences | 29A1.4 | Rat | IgG2a | Alexa 647 | 560755 |
| anti-CD107a | BD Biosciences | 1D4B | rat SD | IgG2a, κ | V450 | 560648 |
| Anti-CD11b | Biolegend | M1/70 | Rat | IgG2b, κ | BV605 | 101237 |
| anti-CD11c | Biolegend | N418 | Hamster | IgG | PE/dazzle | 117347 |
| anti-CD19 | Biolegend | 6D5 | rat | IgG2a, κ | BV510 | 115545 |
| Anti-CD19 | Biolegend | 6D5 | Rat | IgG2a, κ | BV785 | 115543 |
| Anti-CD25 | eBioscience | PC 61.5 | Hamster | IgG1 λ | PE-Cy7 | 25-0251-82 |
| anti-NKp46 | BD HORIZON | 29A1.4 | Rat | IgG2a, κ | BV510 | 563455 |
| anti-CD3e | BD Biosciences | 145-2C11 | Hamster | IgG1, κ | FITC | 553062 |
| Anti-CD3e | Biolegend | 145-C11 | Hamster | IgG | PerCP | 100302 |
| anti-CD4 | BD Biosciences | GK1.5 | rat | IgG2b, κ | PE | 553730 |
| anti-CD4 | LifeTech | monoclonal | rat | IgG2a | PE-AF700 | MCD0424 |
| anti-CD8a | BD Biosciences | 53-6.7 | Rat LOU | IgG2a, κ | PerCP-Cy5.5 | 551162 |
| Anti-F4/80 | Biolegend | BM8 | Rat | IgG2a, κ | PerCP-Cy5.5 | 123128 |
| Anti-F4/80 | Biolegend | BM8 | Rat | IgG2a, κ | BV510 | 123135 |
| Anti-Ly6C | eBiosciences | HK1.4 | rat | IgG2c, κ | APC-eFluor780 | 47-5932-82 |
| Anti-Gr-1 | Biolegend | RB6-8C5 | rat | IgG2b, κ | PE | 108408 |
| Anti-Gr-1 | BD Biosciences | RB6-8C5 | Rat | IgG2b, κ | PE | 553128 |
| Anti-Gr-1 | Biolegend | RB6-8C5 | Rat | IgG2b, κ | BV421 | 108434 |
| Anti-Ly6G | BD Biosciences | 1A8 | Rat LEW | IgG2a, κ | PE-Cy7 | 560601 |
| Anti-Ly6G | Biolegend | 1A8 | Rat | IgG2a, κ | BV421 | 127627 |
| Anti-Ly6G | BD Biosciences | 1A8 | Rat LW | IgG2a, κ | BV711 | 563979 |
| anti-GD3 | Abcam | R24 | mouse | IgG3 | uncoupled | ab11779 |
| Anti-GD3 | Biotem | R24 Hybridoma ATCC HB-8445 | mouse | IgG3 | Uncoupled endotoxin free for in vivo experiment | Hybridoma ATCC HB-8445 |
| Anti-53BP1 | Novus Biological | Rabbit polyclonal | Rabbit | IgG | uncoupled | NB100-305 |
| Recombinant Human Siglec-7 Fc Chimera Protein | R&D Systems | Human recombinant | | | uncoupled | 1138-SL-050 |

GTEX Human Gene Expression Analysis.

The Genotype-Tissue Expression (GTEx) project is an ongoing effort to build a comprehensive public resource to study tissue-specific gene expression and regulation. Samples were collected from 54 non-diseased tissue sites across nearly 1000 individuals. We used the raw open access files from GTEX datasets to extract genes expression and various metainformations such as age, sex or organs origin from the human donor's cohort. We generated a home-made Python script (freely available on demand) that crossed GTEX RNA-seq data with related GTEX annotations files. The script is usable under Windows, Mac or Linux. The output is saved in a single Excel file containing the information for the selected gene. Data were then plotted and statistically analyzed using Prism GraphPad version 8.

Statistical Analysis.

Reasonable sample size was chosen to ensure adequate reproducibility of results and was based on our previous studies. Mouse experiments are performed on n=4 individuals as indicated in Fig legends. Statistical tests were all performed with GraphPad Prism 8 software including the Student's t-test, the Mann-Whitney test, the log-rank test, Pearson correlation, and two-way ANOVA tests.

Results

Aging is defined as a loss of cell and tissue resilience mediated by senescent cell accumulation without knowing precisely why and how they accumulate. Interestingly, the immune system plays a major role in senescent cells elimination, essentially through NK cells, Macrophages and CD4+ T cells[6,7,9,12,13] to maintain homeostasis in a SASP (Senescence Associated Secretory Phenotype) manner. Strikingly, senescent cells can also mediate immunosuppressive properties to block NK cell functions[8,11]. In order to determine key features of senescence immunosurveillance, we analyzed using in vivo matrigel plug assay, the immune recruitment induced by human replicative senescent cells (Data not shown). We cultured the human lung primary fibroblast MRC5 in 5% O2 condition until replicative senescence defined by at least 90% of SA-β-Gal+, EdU− cells (Data not shown) and an increase of DNA Damage and Telomere Induced Foci TIF, (Data not shown). Consistently with previous data[8,9,11,13], the immune infiltrate recruited by human replicative senescent cells is deeply affected with an increase of NK cells (CD3− NKp46+ cells) and neutrophiles (CD11b+ GR1+ cells) infiltration (Data not shown). However, the degranulation of NK cells recruited by senescent cells is three-fold less (Data not shown). We performed the same matrigel plug assay using only the conditioned media from the same cells and observed that the SASP of those senescent cells do not modify the immune infiltrate neither NK cell recruitment or functionality nor myeloid cells ((Data not shown). In in vitro co-culture experiment (Data not shown), we observed that human replicative senescent cells functionally inhibit NK cells degranulation compared to young counterparts but not IFN-γ production (Data not shown). Thus, human replicative senescent cells can inhibit NK cell functionality through a SASP independent mechanism.

Because SASP appeared insufficient to mimic the effect of senescent cells on immune infiltrate and NK cell inhibition (Data not shown), we reasoned that cell surface molecules are probably implicated. We analyzed the glycocalyx composition of control and senescent cells by mass spectrometry with a specific focus for glycolipids, N-glycans and O-glycans (Data not shown). We observed that disialylated O-glycane (m/z 1256, 1501 and 1705) where increased contrary to monosialylated species (m/z 895 and 1344) (Data not shown). No significant modifications of the N-glycome have been observed (Data not shown). More strikingly, we observed a global glycolipids sialylation in human replicative senescent cells. While pd130 cells are composed of neutral globosides (Gb3 and Gb4) and gangliosides (GM3, GM2 and GM1 sialylated), replicative senescent cells consist almost entirely of gangliosides, with the appearance of disialylated gangliosides (GD3) (Data not shown). FACS and immunofluorescence analysis (Data not shown) confirmed this GD3 induction by senescent cells. By measuring ganglioside biosynthesis enzyme expression by qPCR (Data not shown), only ST8SIA1, the enzyme producing GD3, is strongly increased by replicative senescent cells (Data not shown). Surprisingly, the GD3 expression is not a cumulative effect of cell proliferative history but is strongly expressed during the last divisions before senescence entry (Data not shown). Moreover, GD3 is not cleaved or secreted since we were not able to detect any GD3 neither in the supernatant of replicative senescent cells nor in the serum of 24 months-old mice (Data not shown). Interestingly, ST8SIA1 and GD3 expression has also been found in stress induced senescent cells (Data not shown). On the contrary, while ST8SIA1 expression is 4 to 10 times fold increased in replicative senescent WI38 human pulmonary fibroblast or stress-induced senescence (Bleomycin) human mammary epithelial cells (HMEC), ST8SIA1 is strongly repressed in their related OIS cells (Data not shown). Consistently, in lungs of 2 months-old KRasG12D overexpressing mice, OIS cells defined as SA-β-Galactosidase+ cells do not express GD3 (Data not shown). Since GD3 can trigger the inhibitory ITIM receptor Siglec-7[16] (or Siglec-E/H in mice[17]) and regulate strong immunogenic capacities of [18,19], we analyzed the impact of senescent cells that naturally express GD3 (stress induced and replicative senescent cells) or, on the contrary, naturally repress it (OIS) on NK cell functionality in vitro. While OIS cells that do not express GD3 can increase NK cell degranulation (Data not shown), all the senescent cells that express GD3 abolished NK cell degranulation (Data not shown). Therefore, we hypothesized that GD3 expression regulate the capacity of senescent cell to trigger NK cell activation.

To determine whether GD3 expression by senescent cells regulates their immunogenic properties towards NK cells, we modulate GD3 dosage in senescent cells (Data not shown) by enzymatic treatment (neuraminidase; (Data not shown) or ST8SIA1 knock-down (Data not shown) or by overexpressing ST8SIA1 in young cells (Data not shown) before NK cells coculture assay. GD3 abolishment by neuraminidase or by KD of ST8SIA1 totally rescue the capacity of senescent cells to activate NK cells degranulation (FIG. 1A) but do not favor IFN-γ production (Data not shown). Similarly, the overexpression of ST8SIA1 by young dividing cells (Data not shown), which do not induce senescence entry (Data not shown), inhibit NK cell degranulation (Data not shown) and is abolished by neuraminidase treatment (Data not shown). Even if the ST8SIA1 overexpression in young cells can confer the same immunosuppressive capacities than senescent cells, this overexpression is not sufficient to trigger senescence in those cells (Data not shown). Inversely, ST8SIA1 KD in replicative senescent cells is not sufficient to force senescence exit (Data not shown). Taken together, these data suggest that GD3 induction at senescence onset is the consequence of the senescence program but not the event that triggers senescence entry. Since GD3 is a cell surface molecule that can be targetable by antibodies, we address the question whether NK cell degranulation can also be restored using an anti- GD3 monoclonal antibody (FIG. 1B). The GD3 targeting by monoclonal antibody was sufficient to restore NK cell degranulation in a dose-response manner, reaching a full rescue with 2 μg of antibody (Data not shown), probably by inhibiting the interaction between GD3 and the inhibitory receptor Siglec-E/H but also by favoring ADCC20. More than degranulation of murine NK cells, GD3 expression is sufficient to inhibit senescent cell killing by human NK cells (Data not shown). The inhibition of human NK cell killing of human senescent cells is GD3 dependent as revealed by the killing rescue after anti GD3 mAb treatment (Data not shown). Taken together, we revealed that GD3 expression by senescent cells determine their capacity to inhibit NK cells and to escape to NK cell killing.

To assess the physiological impact of the innate immune surveillance bypass by GD3 expressing senescent cells, we analyzed the expression of GD3 by senescent cells in lung fibrosis. Indeed, recent insights in pulmonary fibrosis clearly establish a link between senescent cells accumulation and lung fibrosis[9,21,22] which can be mimicked in mice by intratracheal instillations of bleomycin[23] (Data not shown). As expected, bleomycin instillation induces a progressive lung fibrosis with severe lesions (Data not shown) 21 days after injections with a clear increase in collagen deposition (Data not shown). Those fibrotic areas contain SA-β-Galactosidase+ cells that express GD3 (Data not shown). Using Imaging flow cytometry, we observed that both immune cells (CD45+ cells) end epithelial cells (EpCAM+ CD45− cells) can be SA-β-Galactosidase+ (Data not shown), with a 4.7-fold-increase in SA-β-Galactosidase+ cells frequency for EpCAM+ cells (Data not shown). Beyond lung fibrosis, we observed that senescent cells found in age-related kidney fibrosis are GD3 positive (Data not shown) and that their presence is strongly increase upon aging (Data not shown). Consistently to the bleomycin induced lung fibrosis, the presence of GD3 positive senescent cells was also observed in an experimental mouse kidney fibrosis using Adriamycin treatment (Data not shown), revealing that GD3 expression by senescent cells is not restricted to the lung. Contrary to human lung fibrosis, it has been shown that bleomycin induced fibrosis can partially regress spontaneously. Consistently, we observed that fibrotic lesion partially regresses at day 120 (Data not shown) with a significant decrease in collagen deposition (Data not shown). However, GD3 positive cells are still present 120 days after injury in the remaining fibrotic lesions and the intensity of GD3 expression is not significantly reduced compared to day 21 (Data not shown). Thus, senescent cells are not eliminated and persisted in the tissues within fibrotic sequelae. Since senescent cells expressing GD3 are found in fibrotic lungs, we assessed whether immune infiltrate is affected. By flow cytometry on fibrotic lungs, we revealed that the global immune infiltrate is slightly altered (Data not shown). To assess their functionality, those NK cells where then rechallenge ex-vivo against potent NK cell target (YAC-1 cells) (Data not shown). Interestingly, NK cells from fibrotic lungs are less functional against YAC-1 cells compared to the PBS counterpart. Moreover, the functionality of splenic NK cells from the same mice were assessed simultaneously (Data not shown). At distance from the lung, NK cells functionality is similar between control and treated group suggesting that the presence of GD3 positive senescent cells within lung parenchyma is sufficient to inhibit NK cell degranulation ex vivo locally but not trigger a systemic NK cell inhibition (Data not shown). Thus, we anticipated that GD3 can be a strong target to block the immunosuppressive effect of senescent cell locally. To demonstrate it, we analyzed the impact of GD3 targeting in vivo using mAb by monitoring the overall survival, the fibrosis lesions by μCT imaging, the quantity of senescent cells by flow imaging and immune capacities by flow cytometry (Data not shown). The anti-GD3 treatment significantly improve the overall survival (FIG. 2) and decrease lung fibrosis monitored by the lung weight (Data not shown) and the quantification of lung density by μCT (Data not shown). The follow-up analysis of lung fibrosis overtime for the same mice reveals that the anti-GD3 treatment was sufficient to block the disease progression and for some individuals, to revert it (Data not shown). This was confirmed by histological analysis of lung fibrosis at the end of the treatment and the comparison with μCT imaging (Data not shown). The anti-fibrotic effect of GD3 mAb is associated to a 25% decrease in senescent cells infiltration (Data not shown) while the expression of GD3 on the remaining senescent cells is similar (Data not shown). The fact that the mAb induce a significant but modest senolytic effect suggest that the therapeutic effect is essentially due to a senomorphic effect through the inhibition of GD3 interaction with its receptor. Consistently, although the treatment did not affect the overall proportion of immune cells (Data not shown), the anti-GD3 treatment was sufficient to restore the NK cell degranulation (Data not shown) and activation (Data not shown). In addition, we assess the functional capacities of lung or spleen NK cells ex vivo through YAC-1 rechallenge experiment (Data not shown). While NK cell proportion in lung (Data not shown) or in spleen (Data not shown) is not affected by the treatment, the lung NK cell functionality (degranulation and IFN-γ production) against YAC-1 was strongly enhance ex vivo (Data not shown). On the contrary, the anti-GD3 mAb treatment to not modify spleen NK cell functionality (Data not shown) showing that the NK cell inhibition is local and dependent of the presence of GD3. Thus, we showed that the profibrotic effect of senescent cells in the lung is GD3 dependent and favor the inhibition of NK cell mediated immunosurveillance.

Figures 4A, 4B:
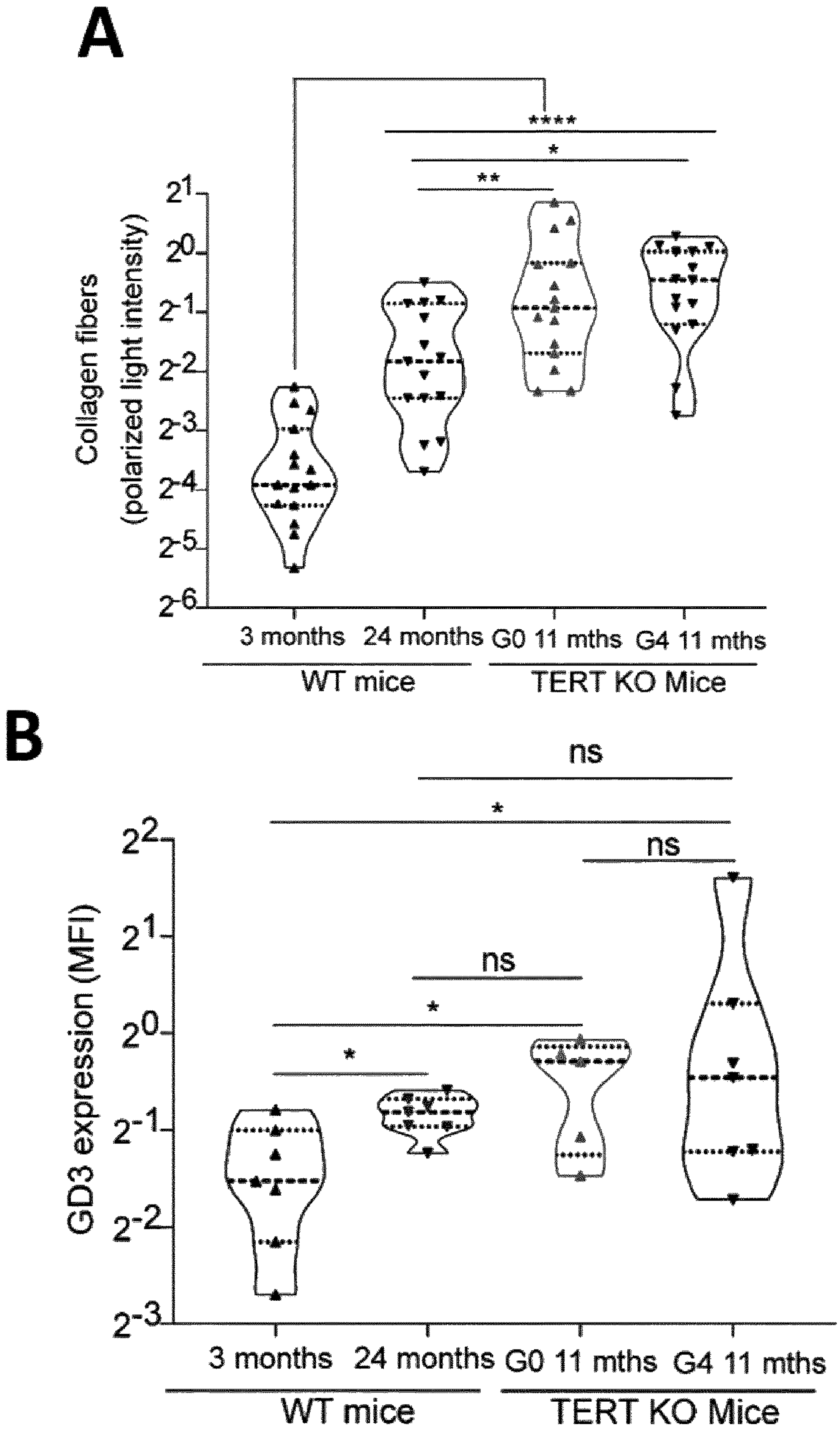

Moreover, we showed increased expression of senescence, ST8SIA1 and pulmonary fibrosis markers in human sequence data (GTEX) upon aging and the correlation between senescence and ST8SIA1; between Senescence and fibrosis and between Fibrosis and ST8SIA1 (FIGS. 3A to 3F). We also demonstrated increased expression of GD3 in old mice and correlation with low-grade pulmonary fibrosis (FIGS. 4A and 4B). Finally, we showed in vitro co-culture experiment showing that pre-exposure of NK cells to GD3+ cells makes NK cells insensitive to a tumor cell and that the addition of the antibody completely removed this inhibition (FIG. 5).

CONCLUSION

In this study, we observed that human replicative senescent cells present strong immunosuppressive function in vivo with abilities to recruit NK cells and to tune their inactivation through a GD3 dependent pathway. This result may explain why replicative senescent cells are not eliminated within tissues during aging and can accumulate with age. Consequently, our results show that senescent cells alter the cell surface glycolipids repertoire conferring thus immunosuppressive capacities and thereby modifying their ability to interact with immune cells. On the contrary, we showed that OIS in human epithelial cells, human fibroblast or mouse lung epithelial cells down-regulate ST8SIA1/GD3 expression, consistently with their capacities to be eliminated by NK. Moreover, we showed that GD3 targeting was sufficient to strongly reduce lung fibrosis and improve overall survival by blunting the senescent cells dependent NK cell inhibition (FIG. 2) in a severe model of lung fibrosis. Taken together, our data give news molecular insight on how senescent cells can regulate their elimination by regulating NK cell mediated immunosurveillance. Systematically, we found that GD3 positive cells inhibit NK cell in vitro and in vivo while GD3 negative is associated with NK cell functionality, both with human or murine cells. Our results bring the proof of concept that GD3 expression may represent a Senescence associated Immune Checkpoint (SIC) that determines senescent cell immunogenicity and identify GD3 and more generally SIC as a multi-hit target for age-associated diseases. Therefore, the identification and the role of SIC on senescence immunosurveillance is a new avenue of research that remains to be explored in depth to develop senescence specific antibodies to force senescence clearance and to attenuate age-associated diseases and cancer.

REFERENCES

Throughout this application, various references describe the state of the art to which this invention pertains. The disclosures of these references are hereby incorporated by reference into the present disclosure.

1. Campisi, J. Aging, Cellular Senescence, and Cancer. Annu Rev Physiol 75, 685-705 (2013).
2. Baker, D. J. et al. Naturally occurring p16Ink4a-positive cells shorten healthy lifespan. Nature 530, 184-189 (2016).
3. Chang, J. et al. Clearance of senescent cells by ABT263 rejuvenates aged hematopoietic stem cells in mice. Nat Med 22, 78-83 (2016).
4. Yosef, R. et al. Directed elimination of senescent cells by inhibition of BCL-W and BCL-XL. Nature Communications 7, 11190 (2016).
5. Gorgoulis, V. et al. Cellular Senescence: Defining a Path Forward. Cell 179, 813-827 (2019).
6. Krizhanovsky, V. et al. Senescence of activated stellate cells limits liver fibrosis. Cell 134, 657-667 (2008).
7. Kang, T.-W. et al. Senescence surveillance of pre-malignant hepatocytes limits liver cancer development. Nature 479, 547-551 (2011).
8. Eggert, T. et al. Distinct Functions of Senescence-Associated Immune Responses in Liver Tumor Surveillance and Tumor Progression. Cancer Cell 30, 533-547 (2016).
9. Ovadya, Y. et al. Impaired immune surveillance accelerates accumulation of senescent cells and aging. Nature Communications 9, 5435 (2018).
10. Muñoz, D. P. et al. Targetable mechanisms driving immunoevasion of persistent senescent cells link chemotherapy-resistant cancer to aging. JCI Insight 4, 328 (2019).
11. Pereira, B. I. et al. Senescent cells evade immune clearance via HLA-E-mediated NK and CD8+ T cell inhibition. Nature Communications 10, 2387 (2019).
12. Xue, W. et al. Senescence and tumour clearance is triggered by p53 restoration in murine liver carcinomas. Nature 445, 656-660 (2007).
13. Iannello, A., Thompson, T. W., Ardolino, M., Lowe, S. W. & Raulet, D. H. p53-dependent chemokine production by senescent tumor cells supports NKG2D-dependent tumor elimination by natural killer cells. 210, 2057-2069 (2013).
14. Talantov, D. Novel Genes Associated with Malignant Melanoma but not Benign Melanocytic Lesions. Clin Cancer Res 11, 7234-7242 (2005).
15. Michaloglou, C. et al. BRAFE600-associated senescence-like cell cycle arrest of human naevi. Nature 436, 720-724 (2005).
16. Hudak, J. E., Canham, S. M. & Bertozzi, C. R. Glycocalyx engineering reveals a Siglec-based mechanism for NK cell immunoevasion. Nature Chemical Biology 10, 69-75 (2014).
17. Zhang, J. Q., Biedermann, B., Nitschke, L. & Crocker, P. R. The murine inhibitory receptor mSiglec-E is expressed broadly on cells of the innate immune system whereas mSiglec-F is restricted to eosinophils. Eur. J. Immunol. 34, 1175-1184 (2004).
18. Nicoll, G. et al. Ganglioside GD3 expression on target cells can modulate NK cell cytotoxicity via siglec-7-dependent and -independent mechanisms. Eur. J. Immunol. 33, 1642-1648 (2003).
19. Büll, C., Heise, T., Adema, G. J. & Boltje, T. J. Sialic Acid Mimetics to Target the Sialic Acid-Siglec Axis. Trends Biochem Sci 41,519-531 (2016).
20. Ortaldo, J. R. et al. Analysis of effector cells in human antibody-dependent cellular cytotoxicity with murine monoclonal antibodies. J Immunol 138,3566-3572 (1987).
21. Boyer, L. et al. Aging-related systemic manifestations in COPD patients and cigarette smokers. PLoS ONE 10, e0121539 (2015).
22. Povedano, J. M. et al. Therapeutic effects of telomerase in mice with pulmonary fibrosis induced by damage to the lungs and short telomeres. Elife 7,185 (2018).
23. Liang, J. et al. Hyaluronan and TLR4 promote surfactant-protein-C-positive alveolar progenitor cell renewal and prevent severe pulmonary fibrosis in mice. Nat Med 22, 1285-1293 (2016).

The invention claimed is:

1. A method for diagnosing and treating a senescent cells accumulation related disease in a subject comprising i) detecting the co-expression of ST8Sia1 with a senescence marker in a biological sample obtained from a subject and ii) and identifying a subject having co-expression of ST8Sia1 and the senescence marker as suffering from a senescent cells accumulation related disease, and iii) administering to said subject a therapeutically effective amount of a GD3 inhibitor.

2. The method according to claim 1, wherein the biological sample is a blood sample, a lymph sample, or a biopsy.

3. The method according to claim 1, wherein the senescent cells accumulation related disease is selected from the group consisting of: arthritis, osteoarthritis, osteoporosis, atherosclerosis, dysplastic or preneoplastic lesions, benign prostatic hyperplasia, normal and/or tumor tissues following DNA-damaging therapy, Alzheimer's disease, Parkinson's disease, cataracts, macular degeneration, glaucoma, atherosclerosis, acute coronary syndrome, myocardial infarction, stroke, hypertension, pulmonary fibrosis, kidney fibrosis, idiopathic pulmonary fibrosis (IPF), chronic obstructive pulmonary disease (COPD), osteoarthritis, osteoporosis, type 2 diabetes, obesity, fat dysfunction, coronary artery disease, cerebrovascular disease, periodontal disease; cancer treatment-related tissue atrophy and fibrosis, brain and heart injury, a therapy-related myelodysplastic syndrome; Hutchinson-Gilford progeria syndrome, Werner syndrome, Cockayne syndrome, exroderma pigmentosum, ataxia telangiectasia, Fanconi anemia, dyskeratosis congenital, aplastic anemia, idiopathic pulmonary fibrosis, a cardiovascular disease, an inflammatory or autoimmune disease, a neurodegenerative disease, diabetic ulcer, metabolic syndrome, a pulmonary disease; a gastrointestinal disease, liver fibrosis, muscle fatigue, oral submucosa fibrosis, pancreatic fibrosis, benign prostatic hyperplasia (BPH), an age-related sleep disorder; male and female reproductive disorders, egg supply, sperm viability, male and female fertility, sex drive, erectile function and arousal; a dermatological disease; diabetic wound healing, post-transplant kidney fibrosis, and carotid thrombosis.

4. The method according to claim 1, wherein the senescent cells accumulation related disease is: idiopathic pulmonary fibrosis (IPF); kidney fibrosis; arthritis; osteoporosis, or chronic obstructive pulmonary disease (COPD).

5. A method for treating senescent cells accumulation related disease in a subject identified as having ST8Sia1 expression, comprising administering to said subject a therapeutically effective amount of a GD3 inhibitor.

6. The method according to claim 5, wherein the GD3 inhibitor is selected from the group consisting of a small organic molecule, a polypeptide, an aptamer, an antibody, an oligonucleotide, a CAR-T cell, a CAR NK cell and a ribozyme.

7. The method according to claim 5, wherein the GD3 inhibitor is a monoclonal antibody.

8. The method of claim 3, wherein the cardiovascular disease is angina, aortic aneurysm, arrhythmia, brain aneurysm, cardiac diastolic dysfunction, cardiac fibrosis, cardiac stress resistance, cardiomyopathy, carotid artery disease, coronary thrombosis, endocarditis, hypercholesterolemia, hyperlipidemia, mitral valve prolapse, or peripheral vascular disease.

9. The method of claim 3, wherein the inflammatory or autoimmune disease is a herniated intervertebral disc, inflammatory bowel disease, kyphosis, oral mucositis, lupus, interstital cystitis, scleroderma or alopecia.

10. The method of claim 3, wherein the dermatological disease is atopic dermatitis, cutaneous lupus, cutaneous lymphomas, dysesthesia, eczema, eczematous eruptions, eosinophilic dermatosis, fibrohistocytic proliferations of skin, hyperpigmentation, immunobullous dermatosis, nevi, pemphigoid, pemphigus, pruritis, psoriasis, rashes, reactive neutrophilic dermatosis, rhytides or urticaria.

* * * * *

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Synthetic hST8SIA1 sense

<400> SEQUENCE: 1

gggtgaggca agttgaaagg                                                    20
```

-continued

```
<210> SEQ ID NO 2
<211> LENGTH: 20
<212> TYPE: DNA
<213> ORGANISM: Artificial Sequence
<220> FEATURE:
<223> OTHER INFORMATION: Synthetic hST8SIA1 antisense

<400> SEQUENCE: 2

aggtcctcag cgaatttcca                                        20


<210> SEQ ID NO 3
<211> LENGTH: 21
<212> TYPE: DNA
<213> ORGANISM: Artificial Sequence
<220> FEATURE:
<223> OTHER INFORMATION: Synthetic RPL0 sense

<400> SEQUENCE: 3

aactctgcat tctcgcttcc t                                      21


<210> SEQ ID NO 4
<211> LENGTH: 21
<212> TYPE: DNA
<213> ORGANISM: Artificial Sequence
<220> FEATURE:
<223> OTHER INFORMATION: Synthetic RPL0 antisense

<400> SEQUENCE: 4

actcgtttgt acccgttgat g                                      21
```